US012710425B2

(12) United States Patent
Lee et al.

(10) Patent No.: US 12,710,425 B2
(45) Date of Patent: Aug. 18, 2026

(54) COMPOSITION FOR CANCER DIAGNOSIS

(71) Applicant: ACURASYSBIO CO., LTD., Seoul (KR)

(72) Inventors: Hyung Keun Lee, Seoul (KR); Dong Ki Lee, Seongnam-si (KR); Sung Ill Jang, Seoul (KR); So Young Kim, Suwon-si (KR); A Reum Yeo, Seoul (KR); Jong Kyoung Kim, Pohang-si (KR); Eun-Ju Chang, Seoul (KR)

(73) Assignee: ACURASYSBIO CO., LTD., Seoul (KR)

( * ) Notice: Subject to any disclaimer, the term of this patent is extended or adjusted under 35 U.S.C. 154(b) by 1111 days.

(21) Appl. No.: 17/595,665

(22) PCT Filed: May 21, 2020

(86) PCT No.: PCT/KR2020/006637

§ 371 (c)(1),
(2) Date: Nov. 22, 2021

(87) PCT Pub. No.: WO2020/235943

PCT Pub. Date: Nov. 26, 2020

(65) Prior Publication Data

US 2022/0326243 A1 Oct. 13, 2022

(30) Foreign Application Priority Data

May 21, 2019 (KR) ........................ 10-2019-0059625
Dec. 18, 2019 (KR) ........................ 10-2019-0169813

(51) Int. Cl.

| | |
|---|---|
| ***G01N 33/57525*** | (2026.01) |
| ***A61P 35/00*** | (2006.01) |
| ***G01N 33/49*** | (2006.01) |
| ***G01N 33/566*** | (2006.01) |
| ***G01N 33/68*** | (2006.01) |
| *A61K 39/00* | (2006.01) |

(52) U.S. Cl.

CPC ........ *G01N 33/57525* (2026.01); *A61P 35/00* (2018.01); *G01N 33/492* (2013.01); *G01N 33/566* (2013.01); *G01N 33/6869* (2013.01); *A61K 39/001119* (2018.08)

(58) Field of Classification Search

CPC ............................................... G01N 33/57438
USPC ........................................................ 435/4.23
See application file for complete search history.

(56) References Cited

U.S. PATENT DOCUMENTS

2010/0173324 A1 7/2010 Mori et al.

FOREIGN PATENT DOCUMENTS

| | | | |
|---|---|---|---|
| EP | 1777523 | A1 | 4/2007 |
| EP | 3015864 | A1 | 5/2016 |
| KR | 10-0819122 | B1 | 4/2008 |
| KR | 10-2012-0082372 | A | 7/2012 |
| KR | 10-2019-0050950 | A | 5/2019 |
| WO | 2005017150 | A1 | 2/2005 |
| WO | 2006110581 | A2 | 10/2006 |
| WO | 2015067969 | A2 | 5/2015 |
| WO | 2018039490 | A1 | 3/2018 |

OTHER PUBLICATIONS

Sakellariou-Thompson et al (Clinical Cancer Reasearch, 2017, 23(23): 7263-7275).*
Vudattu et al (Int J Cancer, 2007, 121: 1512-1519).*
Motylewska et al (Cytokine, 2015, 75: 373-379).*
Rose et al (J Immunol, 2008, 182(12): 7389-7397).*
Birnbaum et al (Oncotarget, 2016, 7(44): 71198-71210).*
C. W. Elston et al., "Pathological prognostic factors in breast cancer. I. The value of histological grade in breast cancer: experience from a large study with long-term follow-up", Histopathology, 1991, pp. 403-410, vol. 19.
Ittai Ben-Porath et al., "An embryonic stem cell-like gene expression signature in poorly differentiated aggressive human tumors", Nature Genetics, May 2008, pp. 499-507, vol. 40, No. 5.
G. Kohler et al., "Derivation of specific antibody-producing tissue culture and tumor lines by cell fusion", European Journal of Immunology, 1976, pp. 511-519, vol. 6.
Tim Clackson et al., "Making antibody fragments using phage display libraries", Nature, Aug. 15, 1991, pp. 624-628, vol. 352.
James D. Marks et al., "By-passing Immunization Human Antibodies from V-gene Libraries Displayed on Phage", J. Mol. Biol., 1991, pp. 581-597, vol. 222.
Peter E. Nielsen et al., "Sequence-selective recognition of DNA by strand displacement with a thymine-substituted polyamide", Science, Dec. 6, 1991, pp. 1497-1500, vol. 254.
Louis C. Bock et al., "Selection of single-stranded DNA molecules that bind and inhibit human thrombin", Nature, Feb. 6, 1992, pp. 564-566, vol. 355.
Felix Hoppe-Seyler et al., "Peptide aptamers: powerful new tools for molecular medicine", J Mol Med, 2000, pp. 426-430, vol. 78.
Barak A. Cohen et al., "An artificial cell-cycle inhibitor isolated from a combinatorial library", Proc. Natl. Acad. Sci, USA, Nov. 1998, pp. 14272-14277, vol. 95.
J Weiler et al., "Anti-miRNA oligonucleotides (AMOs): ammunition to target miRNAs implicated in human disease?", , Gene Therapy, 2006, pp. 496-502, vol. 13.
Atsushi Nishida et al., "Interleukin-32 Expression in the Pancreas", Journal of Biological Chemistry, Jun. 26, 2009, pp. 17868-17876, vol. 284, No. 26.
Behnam Ebrahimi et al., "Cytokines in Pancreatic Carcinoma", Nov. 3, 2004, pp. 2727-2736, vol. 101, No. 12.

(Continued)

*Primary Examiner* — Sean E Aeder
(74) *Attorney, Agent, or Firm* — Sughrue Mion, PLLC

(57) ABSTRACT

The present disclosure relates to a composition capable of diagnosing cancer, specifically pancreatic cancer or the like, a diagnostic kit comprising the same, and a method of providing information for diagnosis using the composition. Also, the present disclosure relates to a pharmaceutical composition capable of preventing or treating pancreatic cancer.

1 Claim, 23 Drawing Sheets

Specification includes a Sequence Listing.

(56) References Cited

OTHER PUBLICATIONS

Paula Ghaneh et al., “Molecular prognostic markers in pancreatic cancer”, J Hepatobiliary Pancreat Surg 2002, pp. 1-11, vol. 9.
Jannie Borst et al., “CD27 and CD70 in T cell and B cell activation”, Current Opinion in Immunology, 2005, pp. 275-281, vol. 17.
International Search Report for PCT/KR2020/006637 dated Aug. 26, 2020 [PCT/ISA/210].

* cited by examiner

[FIG. 1]
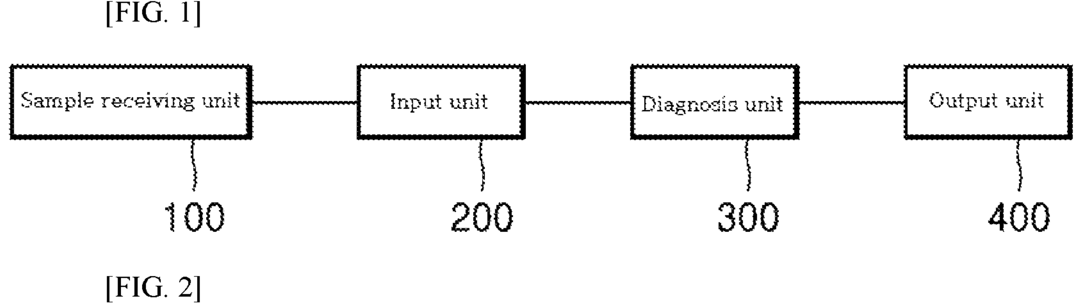
[FIG. 2]
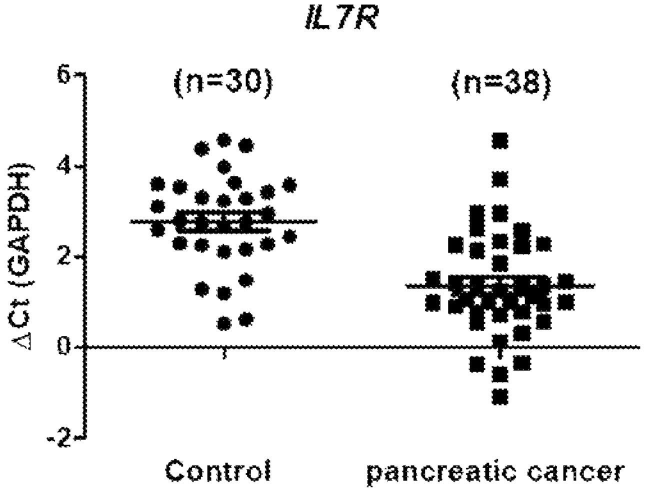

[FIG. 3]
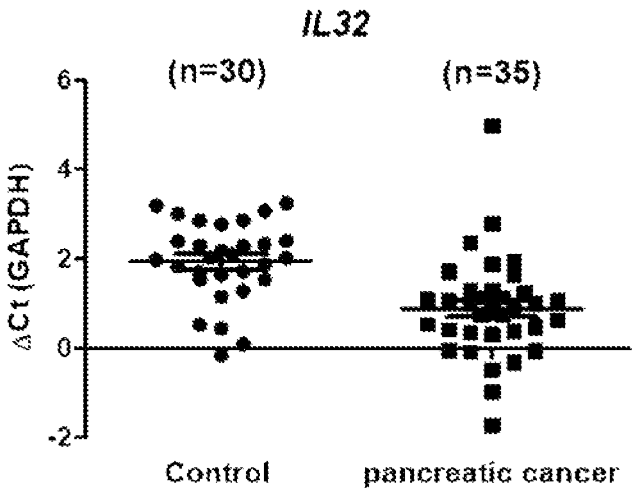
[FIG. 4]
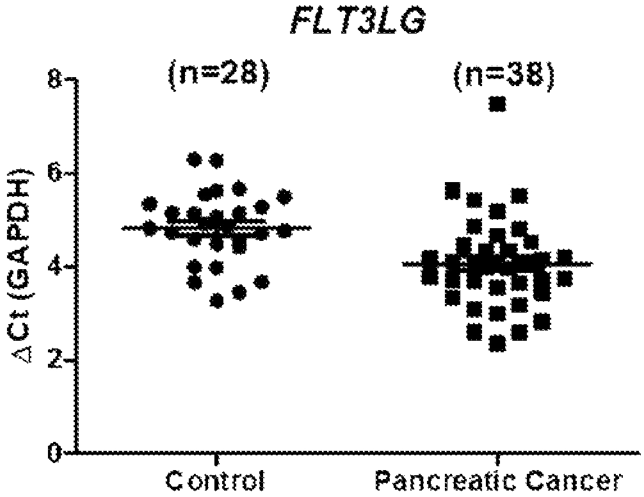

[FIG. 5]
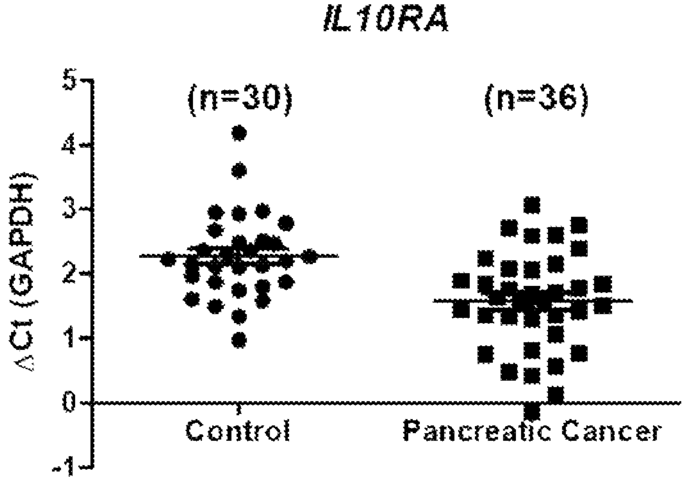
[FIG. 6]
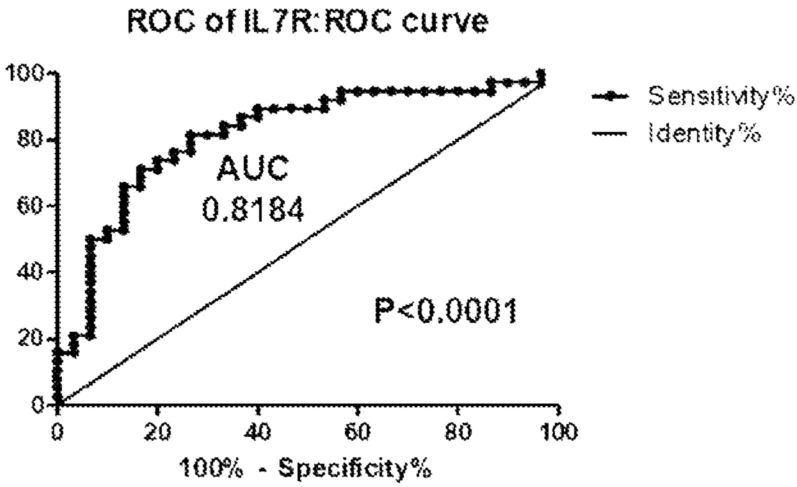

[FIG. 7]
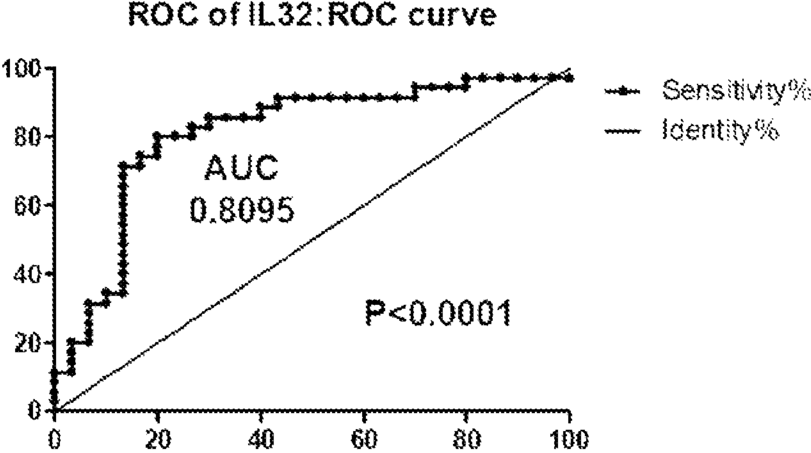
[FIG. 8]
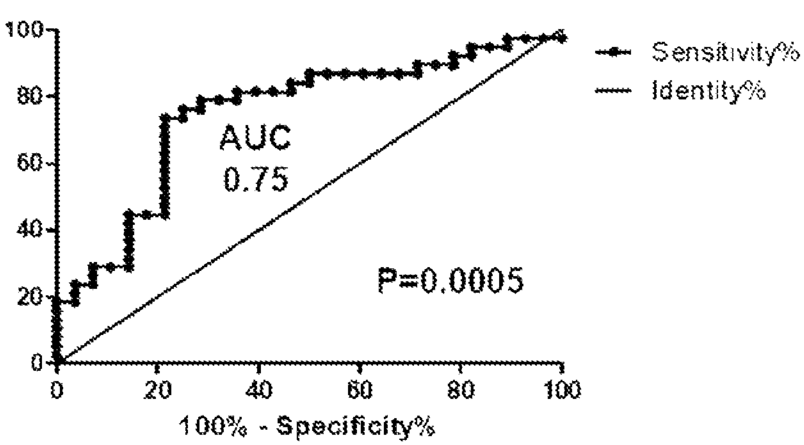

[FIG. 9]
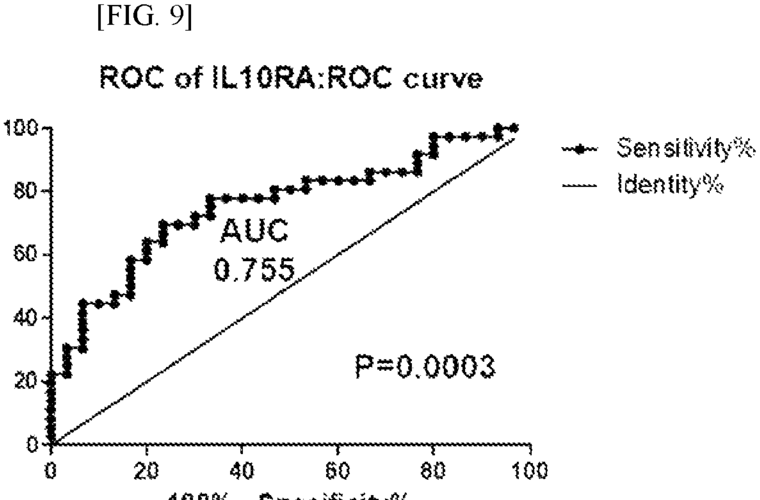
[FIG. 10]
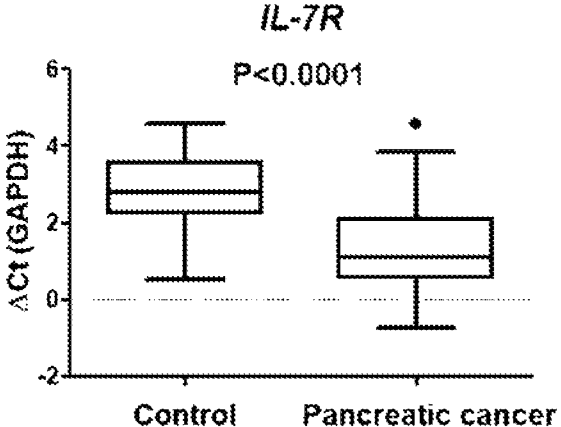

[FIG. 11]
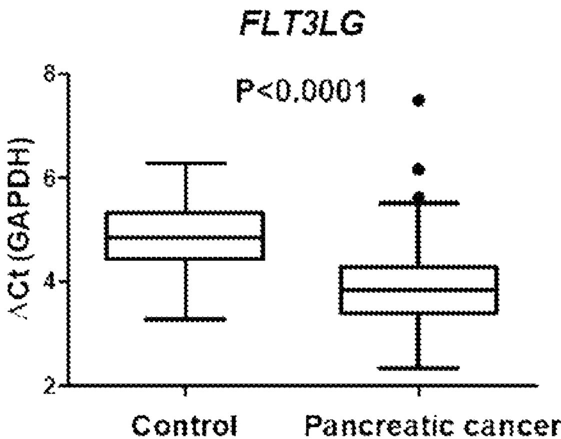
[FIG. 12]
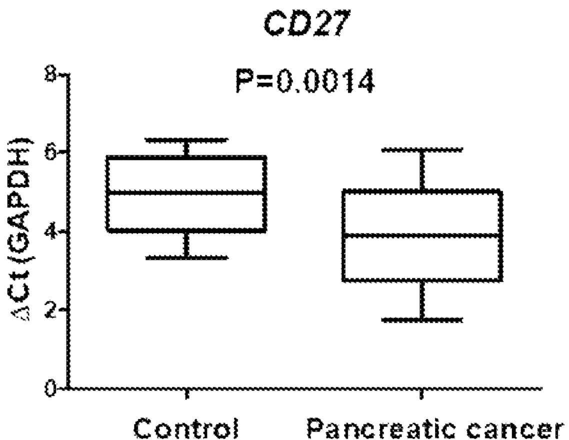

[FIG. 13]
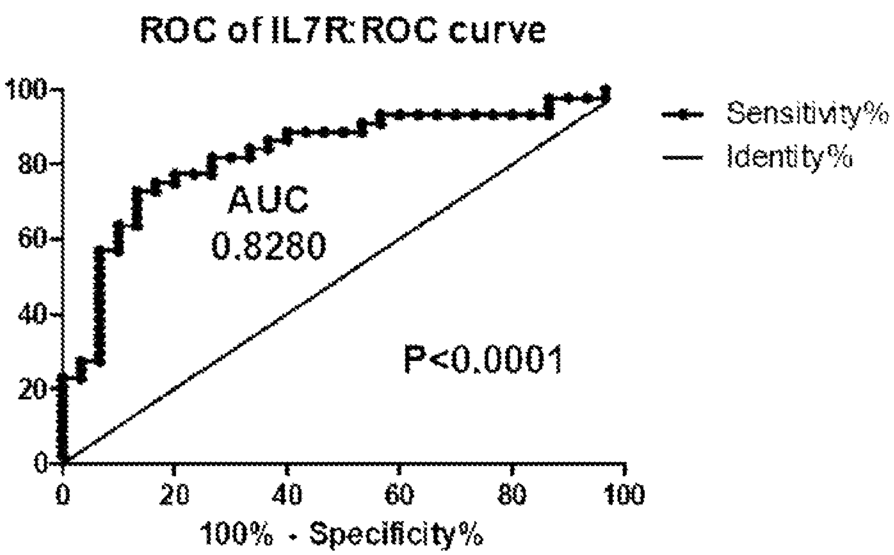
[FIG. 14]
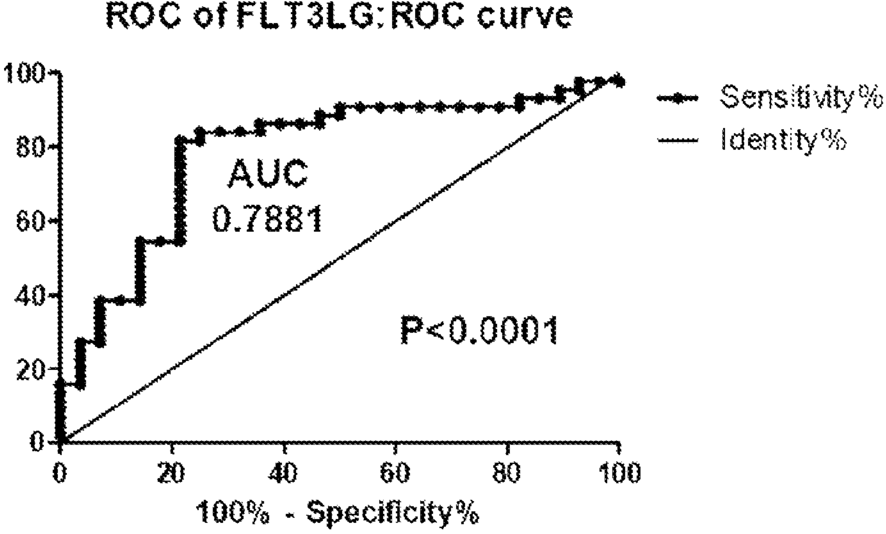

[FIG. 15]
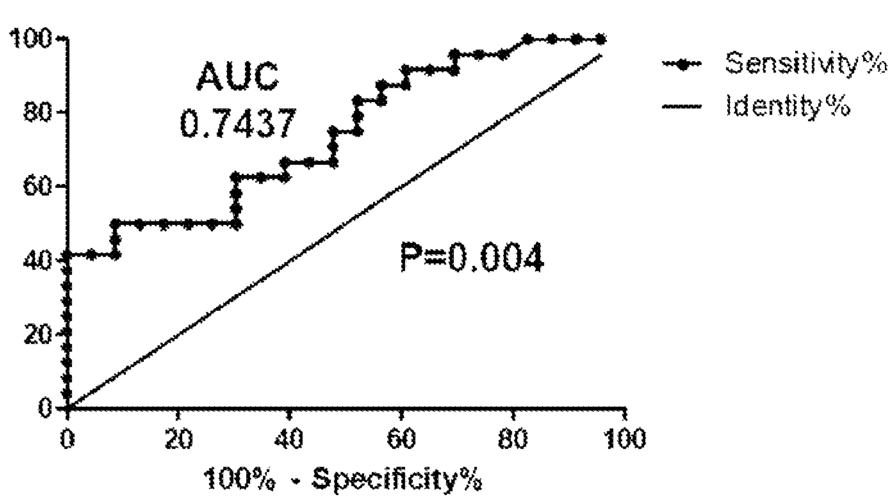
[FIG. 16]
PBS
: Pancreas
Group A. Naïve group : C57BL/6 WT
Pan02 cells
Group B. Pan02 tumor group : C57BL/6 WT + Pan02
Tumor injection — Sacrifice
0 2 4 5 7 11 (day after surgery)
FACS : IL-7R, IL22R1, IL10R2
(quantitation of marker expressed cells in PBMC

[FIG. 17]
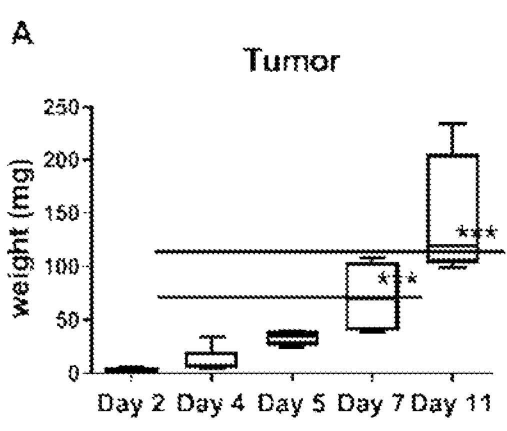
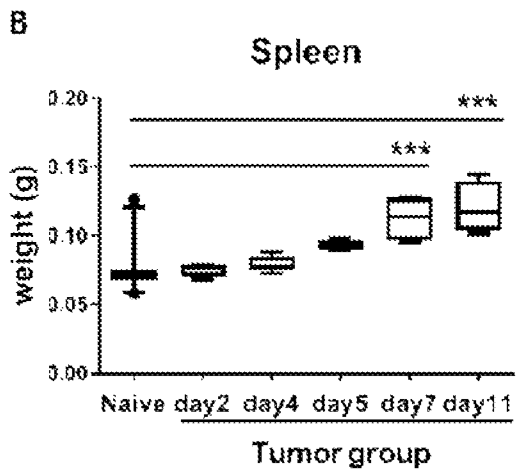
[FIG. 18]
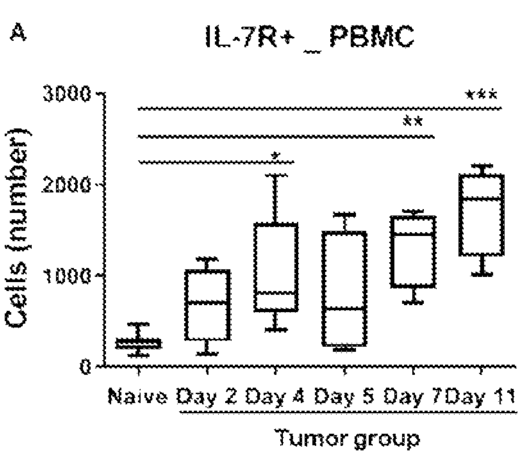
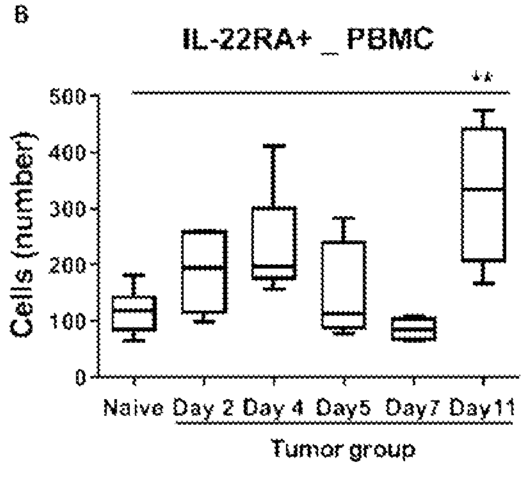
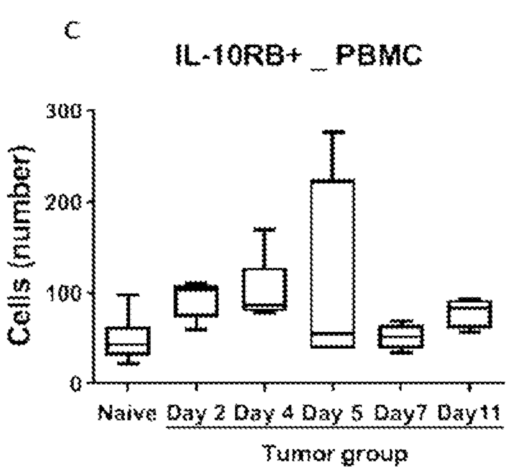

[FIG. 19]
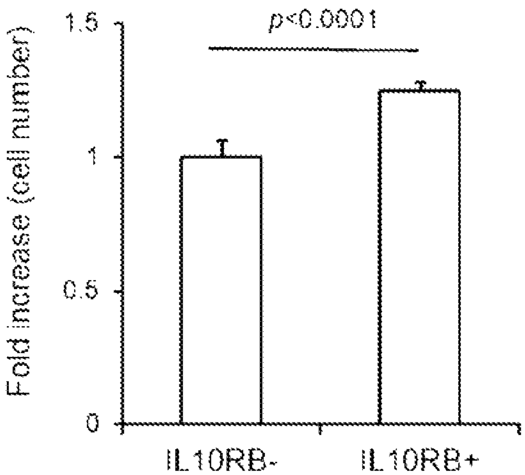
[FIG. 20]
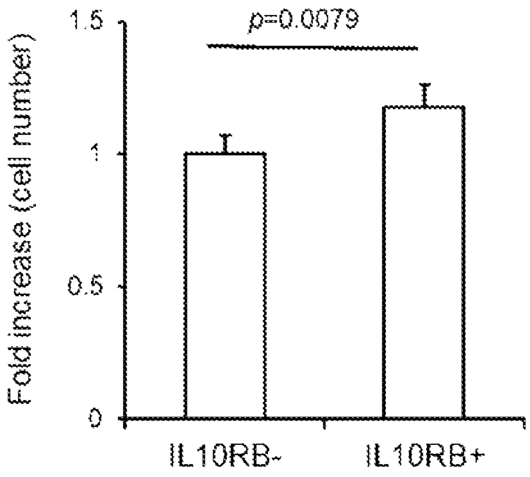

[FIG. 21]
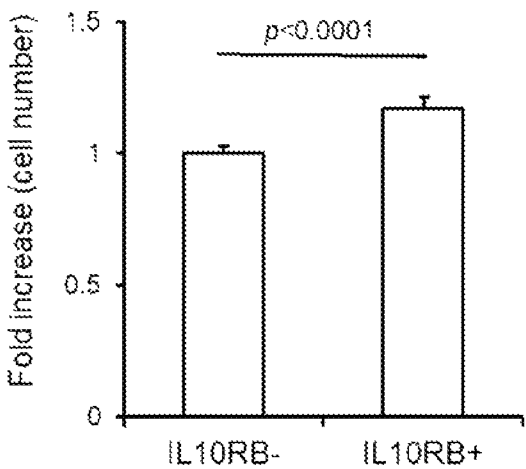
[FIG. 22]
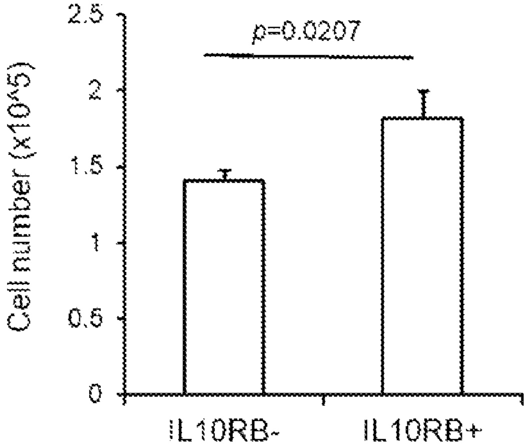

[FIG. 23]
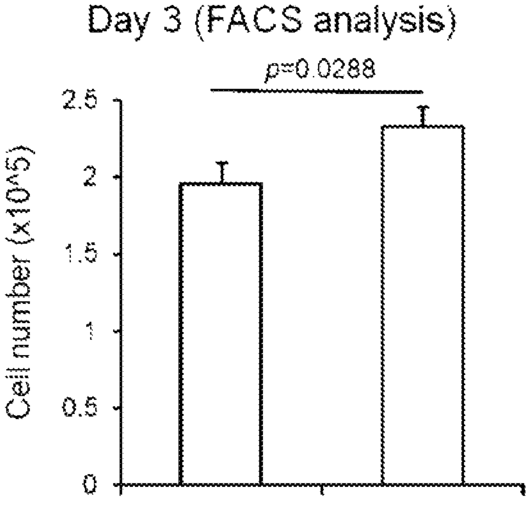
[FIG. 24]
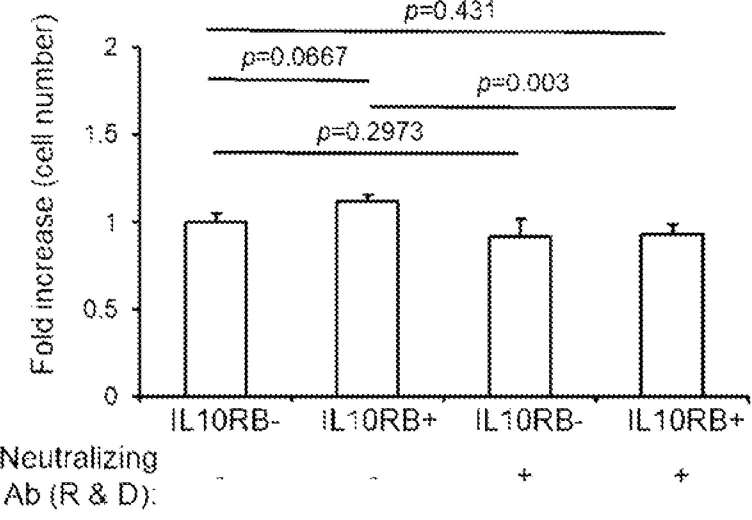

[FIG. 25]
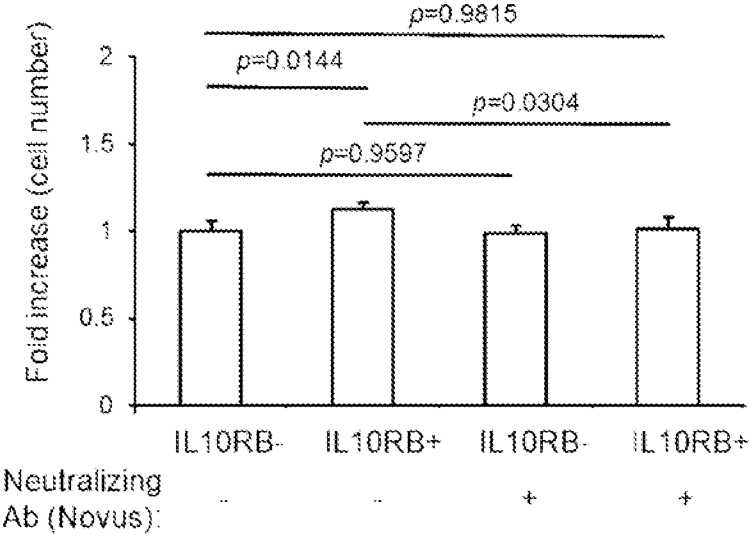
[FIG. 26]
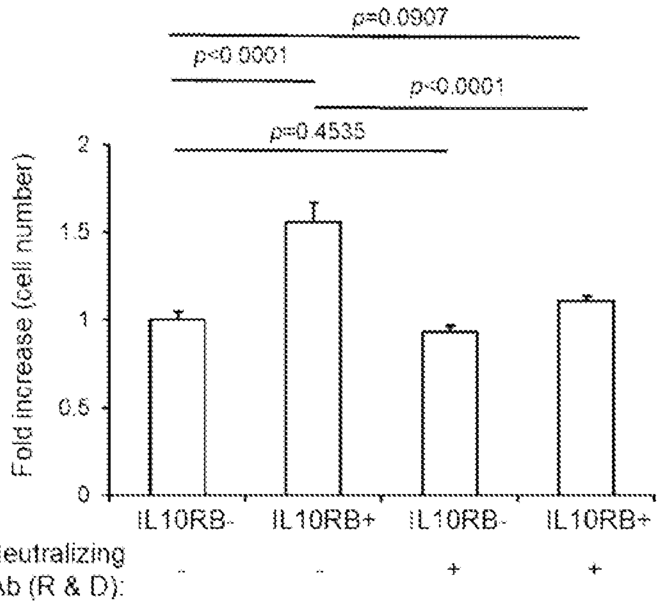

[FIG. 27]
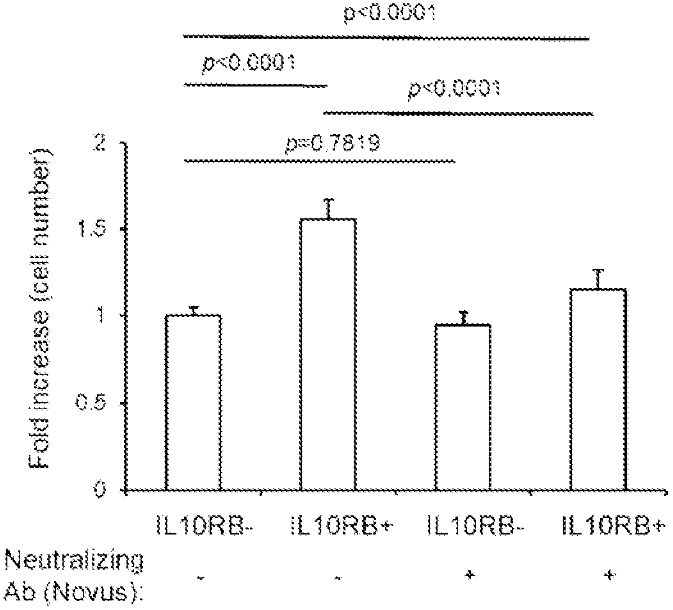
[FIG. 28]
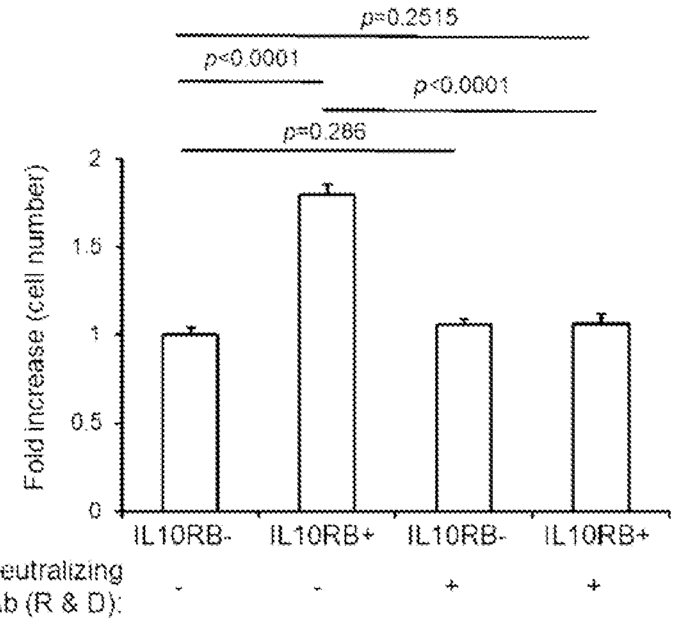

[FIG. 29]
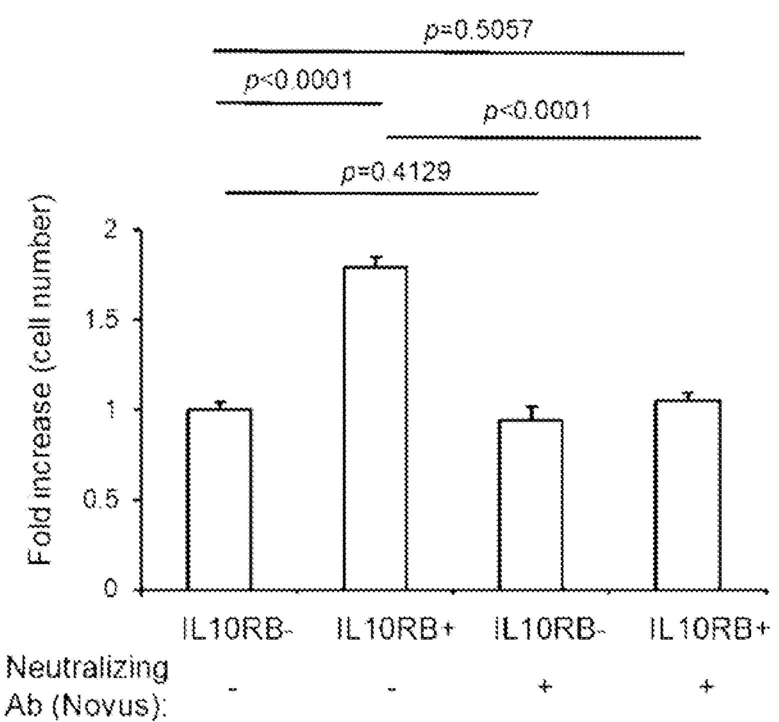

[FIG. 30]
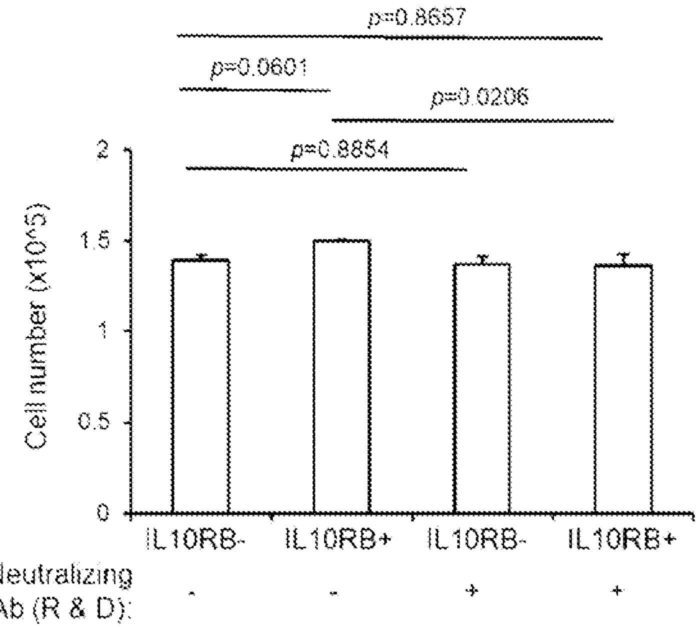
[FIG. 31]
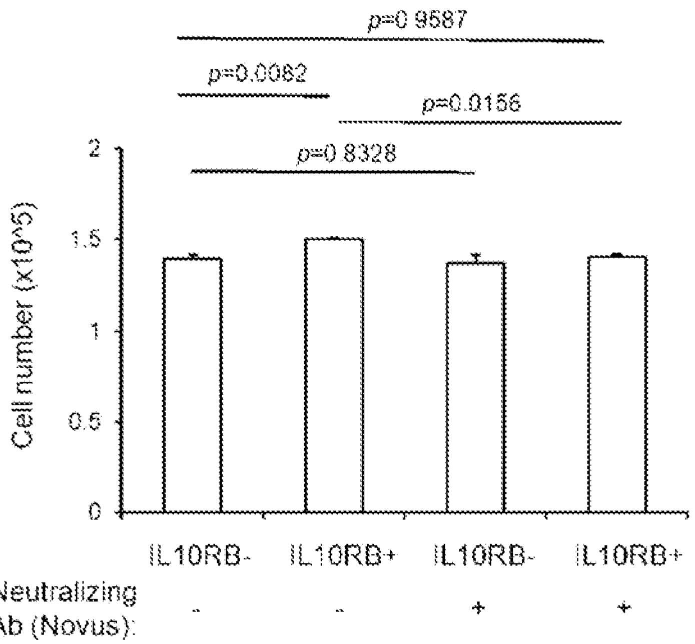

[FIG. 32]
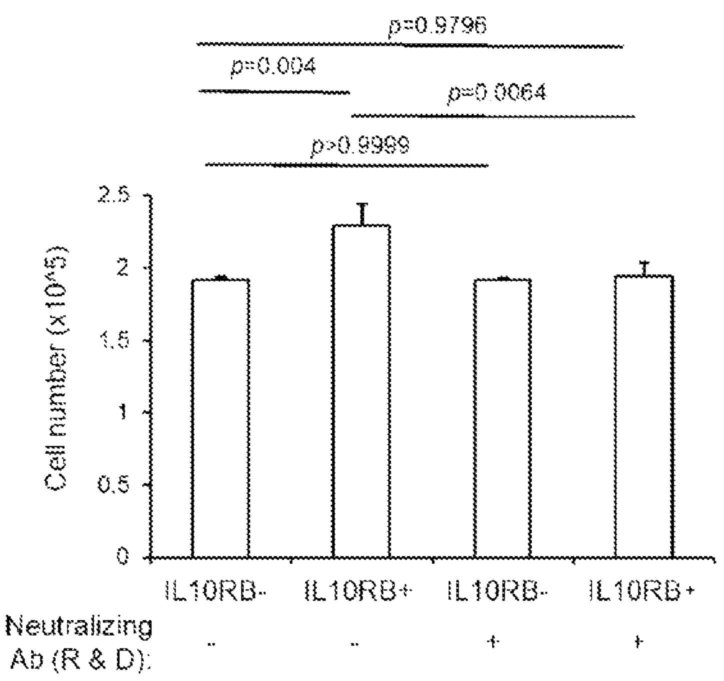

[FIG. 33]
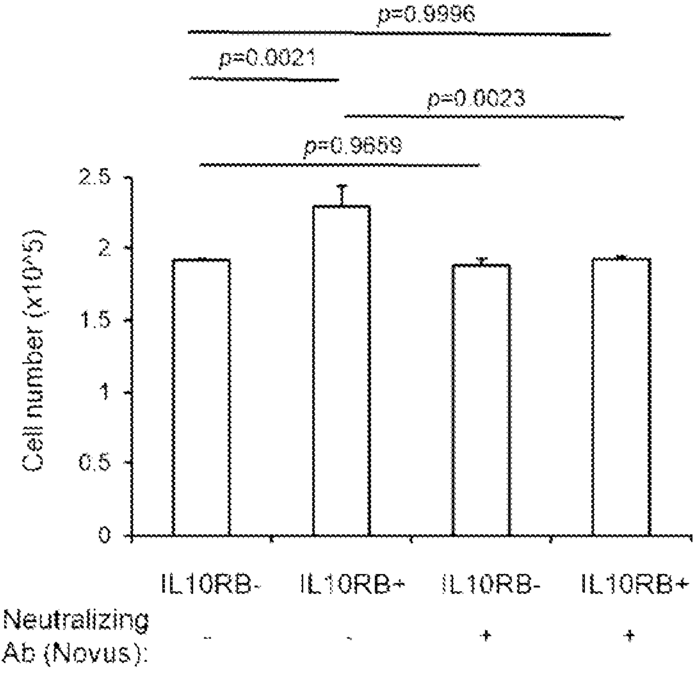
[FIG. 34]
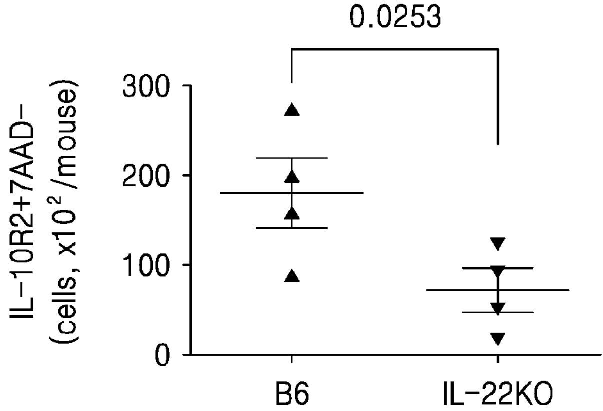

[FIG. 35]
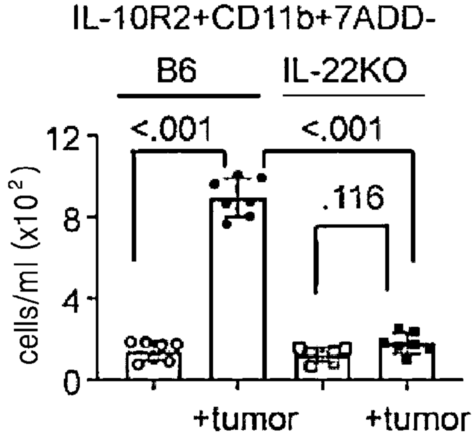
[FIG. 36]
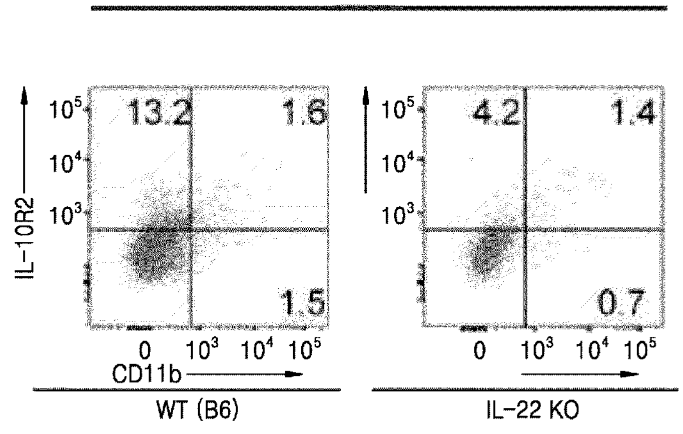

[FIG. 37]
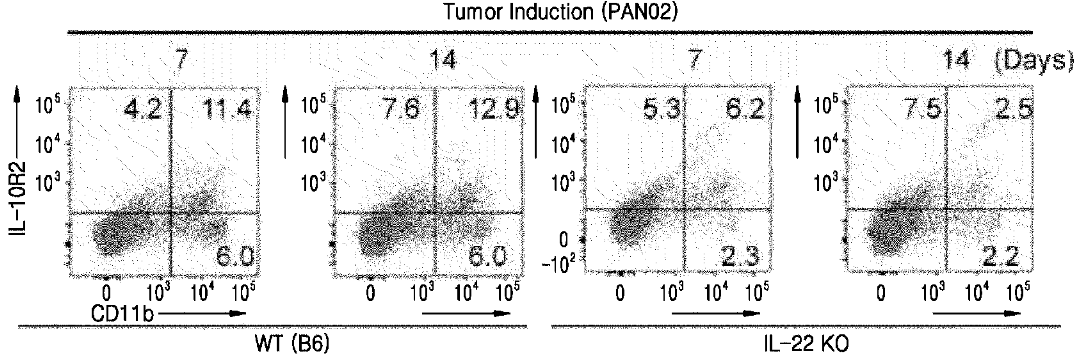
[FIG. 38]
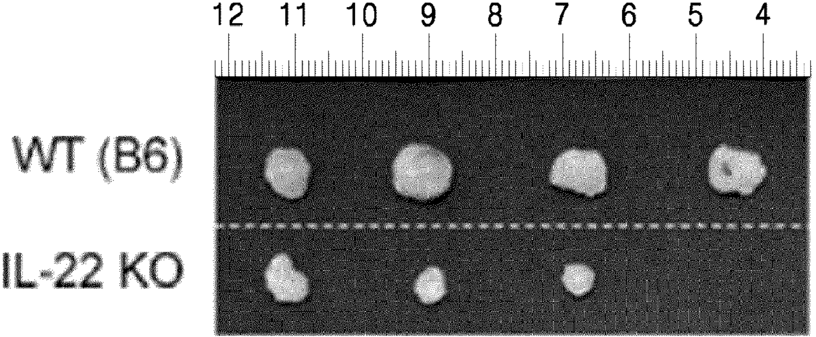

[FIG. 39]
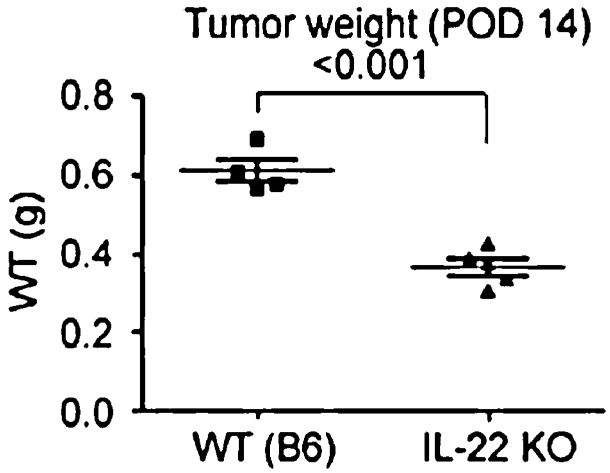
[FIG. 40]
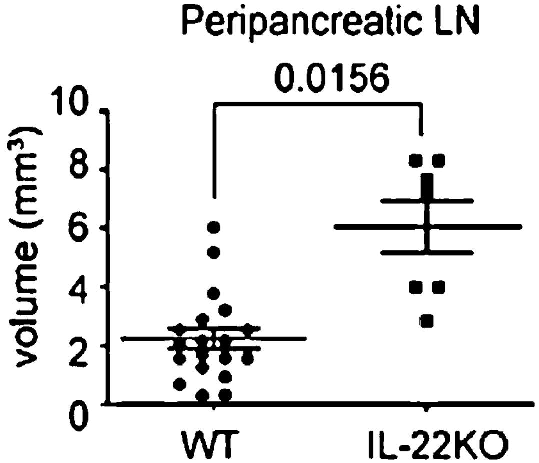

[FIG. 41]
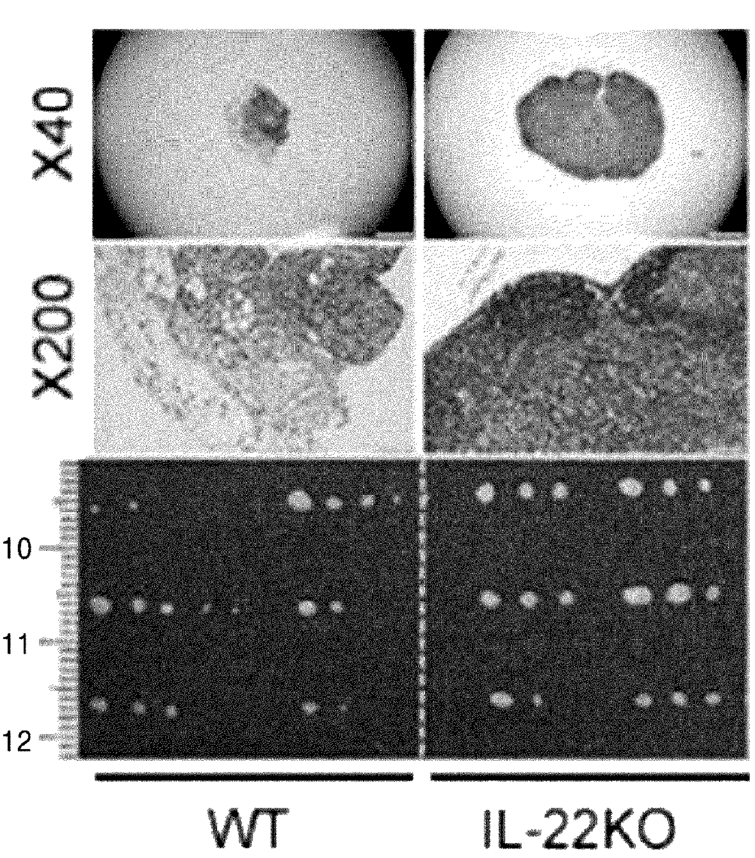

[FIG. 42]
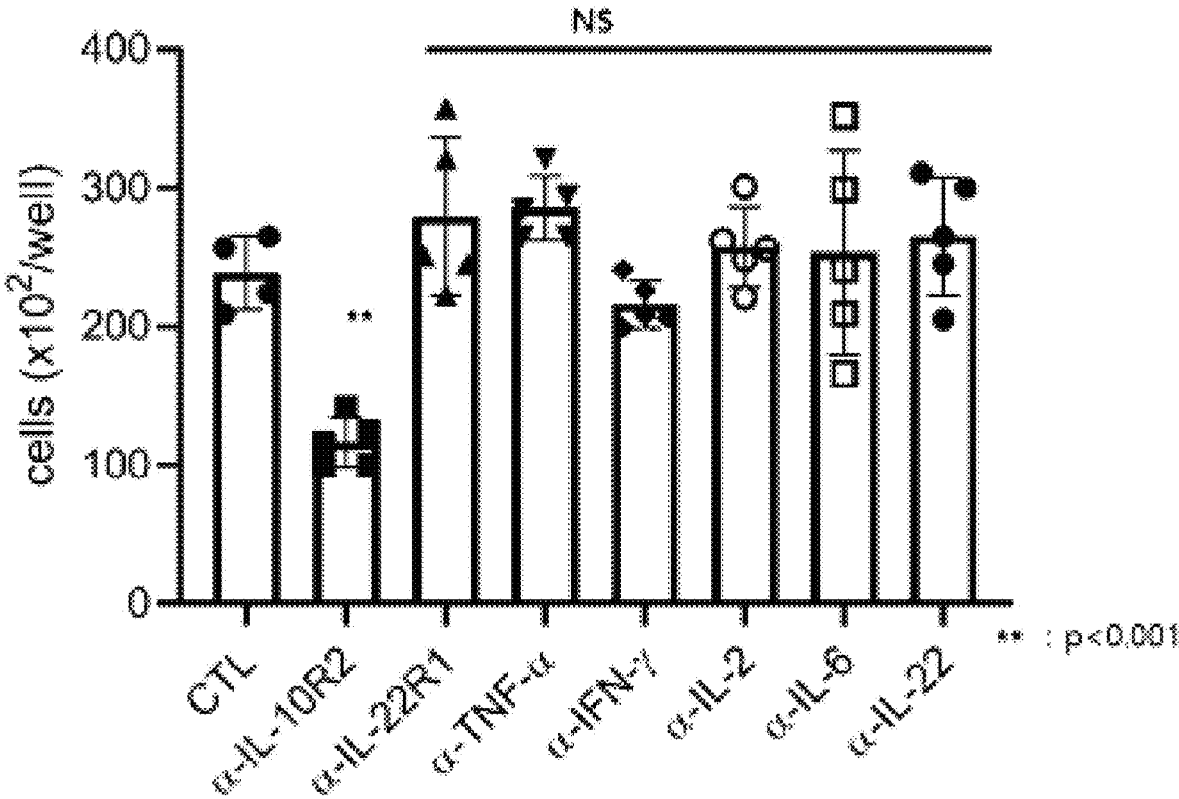

SEQUENCE LISTING

<160> NUMBER OF SEQ ID NOS: 14

<210> SEQ ID NO 1

```
<211> LENGTH: 260
<212> TYPE: PRT
<213> ORGANISM: homo sapiens

<400> SEQUENCE: 1

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260


<210> SEQ ID NO 2
<211> LENGTH: 235
<212> TYPE: PRT
<213> ORGANISM: homo sapiens

<400> SEQUENCE: 2

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80
```

```
Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Ile Leu Leu Leu
            180                 185                 190

Pro Val Gly Leu Leu Leu Leu Ala Ala Ala Trp Cys Leu His Trp Gln
        195                 200                 205

Arg Thr Arg Arg Arg Thr Pro Arg Pro Gly Glu Gln Val Pro Pro Val
    210                 215                 220

Pro Ser Pro Gln Asp Leu Leu Leu Val Glu His
225                 230                 235


<210> SEQ ID NO 3
<211> LENGTH: 459
<212> TYPE: PRT
<213> ORGANISM: homo sapiens

<400> SEQUENCE: 3

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Ile Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
```

```
    210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
        275                 280                 285

Lys Pro Arg Lys Asn Leu Asn Val Ser Phe Asn Pro Glu Ser Phe Leu
    290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
            340                 345                 350

Asp Val Val Ile Thr Pro Glu Ser Phe Gly Arg Asp Ser Ser Leu Thr
        355                 360                 365

Cys Leu Ala Gly Asn Val Ser Ala Cys Asp Ala Pro Ile Leu Ser Ser
    370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
            420                 425                 430

Gln Gly Gln Pro Ile Leu Thr Ser Leu Gly Ser Asn Gln Glu Glu Ala
        435                 440                 445

Tyr Val Thr Met Ser Ser Phe Tyr Gln Asn Gln
    450                 455


<210> SEQ ID NO 4
<211> LENGTH: 234
<212> TYPE: PRT
<213> ORGANISM: homo sapiens

<400> SEQUENCE: 4

Met Cys Phe Pro Lys Val Leu Ser Asp Asp Met Lys Lys Leu Lys Ala
1               5                   10                  15

Arg Met Val Met Leu Leu Pro Thr Ser Ala Gln Gly Leu Gly Ala Trp
            20                  25                  30

Val Ser Ala Cys Asp Thr Glu Asp Thr Val Gly His Leu Gly Pro Trp
        35                  40                  45

Arg Asp Lys Asp Pro Ala Leu Trp Cys Gln Leu Cys Leu Ser Ser Gln
    50                  55                  60

His Gln Ala Ile Glu Arg Phe Tyr Asp Lys Met Gln Asn Ala Glu Ser
65                  70                  75                  80

Gly Arg Gly Gln Val Met Ser Ser Leu Ala Glu Leu Glu Asp Asp Phe
                85                  90                  95

Lys Glu Gly Tyr Leu Glu Thr Val Ala Ala Tyr Tyr Glu Glu Gln His
            100                 105                 110

Pro Glu Leu Thr Pro Leu Leu Glu Lys Glu Arg Asp Gly Leu Arg Cys
        115                 120                 125
```

-continued

```
Arg Gly Asn Arg Ser Pro Val Pro Asp Val Glu Asp Pro Ala Thr Glu
    130                 135                 140

Glu Pro Gly Glu Ser Phe Cys Asp Lys Val Met Arg Trp Phe Gln Ala
145                 150                 155                 160

Met Leu Gln Arg Leu Gln Thr Trp Trp His Gly Val Leu Ala Trp Val
                165                 170                 175

Lys Glu Lys Val Val Ala Leu Val His Ala Val Gln Ala Leu Trp Lys
            180                 185                 190

Gln Phe Gln Ser Phe Cys Cys Ser Leu Ser Glu Leu Phe Met Ser Ser
        195                 200                 205

Phe Gln Ser Tyr Gly Ala Pro Arg Gly Asp Lys Glu Glu Leu Thr Pro
    210                 215                 220

Gln Lys Cys Ser Glu Pro Gln Ser Ser Lys
225                 230


<210> SEQ ID NO 5
<211> LENGTH: 21
<212> TYPE: DNA
<213> ORGANISM: Artificial Sequence
<220> FEATURE:
<223> OTHER INFORMATION: IL-7R Forward Primer

<400> SEQUENCE: 5

gtagtcatca ctccagaaag c                                                21


<210> SEQ ID NO 6
<211> LENGTH: 21
<212> TYPE: DNA
<213> ORGANISM: Artificial Sequence
<220> FEATURE:
<223> OTHER INFORMATION: IL-7R Reverse Primer

<400> SEQUENCE: 6

acctggaaga ggagagaata g                                                21


<210> SEQ ID NO 7
<211> LENGTH: 23
<212> TYPE: DNA
<213> ORGANISM: Artificial Sequence
<220> FEATURE:
<223> OTHER INFORMATION: IL32 Forward Primer

<400> SEQUENCE: 7

cagagctcac tcctctactt gaa                                              23


<210> SEQ ID NO 8
<211> LENGTH: 23
<212> TYPE: DNA
<213> ORGANISM: Artificial Sequence
<220> FEATURE:
<223> OTHER INFORMATION: IL32 Reverse Primer

<400> SEQUENCE: 8

gaaccatctc atgaccttgt cac                                              23


<210> SEQ ID NO 9
<211> LENGTH: 21
<212> TYPE: DNA
<213> ORGANISM: Artificial Sequence
<220> FEATURE:
<223> OTHER INFORMATION: IL10RA Forward Primer

<400> SEQUENCE: 9
```

-continued

```
acttcagcct cctaacctct g                                              21


<210> SEQ ID NO 10
<211> LENGTH: 22
<212> TYPE: DNA
<213> ORGANISM: Artificial Sequence
<220> FEATURE:
<223> OTHER INFORMATION: IL10RA Reverse Primer

<400> SEQUENCE: 10

agggagatgc actcctcttt ag                                             22


<210> SEQ ID NO 11
<211> LENGTH: 20
<212> TYPE: DNA
<213> ORGANISM: Artificial Sequence
<220> FEATURE:
<223> OTHER INFORMATION: FLT3LG Forward Primer

<400> SEQUENCE: 11

tggagcccaa caacctatct                                                20


<210> SEQ ID NO 12
<211> LENGTH: 22
<212> TYPE: DNA
<213> ORGANISM: Artificial Sequence
<220> FEATURE:
<223> OTHER INFORMATION: FLT3LG Reverse Primer

<400> SEQUENCE: 12

tagtcagaca gctcacggat tt                                             22


<210> SEQ ID NO 13
<211> LENGTH: 22
<212> TYPE: DNA
<213> ORGANISM: Artificial Sequence
<220> FEATURE:
<223> OTHER INFORMATION: CD27 Forward Primer

<400> SEQUENCE: 13

gaaggactgt gaccagcata ga                                             22


<210> SEQ ID NO 14
<211> LENGTH: 23
<212> TYPE: DNA
<213> ORGANISM: Artificial Sequence
<220> FEATURE:
<223> OTHER INFORMATION: CD27 Reverse Primer

<400> SEQUENCE: 14

cgaacgagaa gaccagagtt aca                                            23
```

COMPOSITION FOR CANCER DIAGNOSIS

CROSS-REFERENCE TO RELATED APPLICATIONS

This application is a National Stage of International Application No. PCT/KR2020/006637 filed May 21, 2020, which claims priority to Korean Patent Application No. 10-2019-0059625 filed May 21, 2019 and Korean Patent Application No. 10-2019-0169813 filed Dec. 18, 2019, the entire disclosures of which are incorporated herein by reference.

TECHNICAL FIELD

The disclosure relates to a composition capable of diagnosing cancer, particularly pancreatic cancer or the like, a diagnostic kit comprising the same, and a method of providing information for diagnosis using the composition. This patent application claims priorities to Korean Patent Application No. 10-2019-0059625, filed with the Korean Intellectual Property Office on May 21, 2019, and Korean Patent Application No. 10-2019-0169813, filed with the Korean Intellectual Property Office on Dec. 18, 2019, the disclosures of which are incorporated herein by reference.

BACKGROUND ART

Studies on treatment methods and diagnostic methods for cancer among major diseases in modern people, have been relatively actively conducted focusing on lung cancer, liver cancer, gastric cancer, and the like, which have a high incidence. However, studies on esophageal cancer, colorectal cancer, pancreatic cancer, etc. with a low incidence are relatively insufficient.

In particular, pancreatic cancer does not cause noticeable symptoms in the early stages, and usually shows symptoms such as pain and weight loss after systemic metastasis thereof has already occurred, and thus the cure rate thereof is relatively low. Regular screening for pancreatic cancer is very important. Most of the clinical symptoms thereof develop slowly, the patients are prone to weakness, and loss of appetite and weight loss are the most common symptoms. Pancreatic cancer is a fatal cancer with a 5-year survival rate of 1-4% and a median survival period of 5 months, and has the poorest prognosis among all human cancers. 80% to 90% of pancreatic cancer patients are diagnosed in a state in which curative resection enabling complete cure is impossible. For this reason, pancreatic cancer has a poor prognosis, and treatment thereof relies mainly on chemotherapy. Thus, there is an urgent need for the development of a method for early diagnosis of pancreatic cancer more than any other human cancers.

The therapeutic effects of several anticancer drugs, including 5-fluorouracil, gemcitabine and Tarceva, which are currently known to be effective against pancreatic cancer, are extremely poor, and the rate of response to chemotherapy is only about 15%. This suggests that more effective early diagnosis methods and treatment methods are urgently needed in order to improve the prognosis of pancreatic cancer patients. Appropriate diagnosis and treatment for a precancerous lesion of pancreatic cancer, which is a stage prior to fatal pancreatic cancer, is very important for improving the outcome of pancreatic cancer treatment.

Diagnosis of pancreatic cancer or a precancerous lesion of pancreatic cancer is performed by a blood test (CA19-9), X-ray radiography of the stomach and duodenum, cholangiography via the skin and liver, endoscopic retrograde cholangiography, or the like. Lesions of the disease have been detected by these methods, but in recent years, ultrasonography and computed tomography have been most frequently used. A more precise biopsy may also be performed to obtain a relatively accurate test result. However, these diagnostic methods have low accuracy or are very inconvenient to perform, causing pain to patients, and thus subjects are reluctant to undergo such diagnostic methods. Therefore, there has been a need for the development of examination methods capable of simply and rapidly diagnosing pancreatic cancer or precancerous lesion of pancreatic cancer.

Korean Patent No. 10-0819122 and Korean Patent Application Publication No. 2012-0082372 disclose techniques that are performed using various pancreatic cancer markers, including matrilin, transthyretin, stratifin, and the like. However, the different markers show a large difference in their diagnostic efficiency and accuracy, and hence there is a need to discover a marker having a better effect and develop a diagnostic method using the same.

DISCLOSURE

Technical Problem

An object of the present disclosure is to provide a composition or kit capable of diagnosing pancreatic cancer simply and accurately.

Another object of the present disclosure is to provide a method for providing information for diagnosing pancreatic cancer.

Still another object of the present disclosure is to provide a pharmaceutical composition capable of preventing or treating pancreatic cancer.

Yet another object of the present disclosure is to provide an apparatus for diagnosing pancreatic cancer.

However, objects to be achieved by the present disclosure are not limited to the objects mentioned above, and other objects not mentioned herein will be clearly understood by those skilled in the art from the following description.

Technical Solution

One embodiment of the present disclosure is directed to: a biomarker for diagnosing pancreatic cancer comprising at least one protein selected from the group consisting of CSF1R, CXCL16, TNFRSF1B, CX3CR1, CSF3R, TNFRSF14, TNFSF13B, TNF, PPBP, TNFSF10, FLT3LG, TNFRSF8, IL10RA, CKLF, IL12RB1, CXCL10, LTBR, PF4, CD40, IFNGR1, IFNAR1, IL2RG, IL1B, IL15, CD27, EBI3, RETN, IL7R, CCR2, IL16, IL21R, IL2RB, CCR5, IFNAR2, XCL2, IL32, TGFB1, IFNGR2, IL13RA1, CCL3, CD4, TNFSF4, EPOR, TNFRSF17, IL3RA, MIF, CXCR4, TNFRSF18, CMTM6, CMTM7, TNFSF12, IL23A, TGFB3, XCL1, IL27, CXCL3, CCL5, CCL4L2, IL7, HGF, KIT, CD40LG, IL6ST, IL6R, CD70, MST1, CXCL2, TNFSF14, FLT3, IL1R2, TGFBR2, IL6, LIF, CXCR6, CXCL1, CCR7, CXCL11, GDF15, IL1RN, TNFRSF4, CSF1, IL11RA, TNFSF8, IL15RA, CCL2, TNFRSF10A, CXCL8, CCL8, FAS, CCR4, CCL23, ACKR3, TNFSF18, LTA, CCR10, CLCF1, CCL4, IL9R, TGFBR1, TNFRSF10B, CSF2RB, TGFA, CXCL9, TNFRSF1A, OSM, IL4R, PF4V1, PDGFB, CCL20, IL12RB2, CCL25, TGFBR3, IL17RA, IL2RA, TNFRSF10C, CXCR3, IL20RB, CXCL5, IL5RA, CXCR5, TNFRSF11A, IL24, SPP1, CCL22, CCR9, CCL26, CX3CL1, CXCL12, CMTM1, TNFRSF10D, CCR3, CXCR1, CCL3L3, CXCR2, IFNL1, IL18R1, TNFSF15, CCR1, TNFRSF13B, TNFSF13, IL18, FASLG, IFNG, PDGFRB, TNFRSF25, XCR1, IL1R1, TNFRSF9, IL12A, CSF2RA, IL17C, IL2, IL26, IL4, PDGFA, TNFSF11, TNFSF9, CCR6, CCL19, MST1R, TNFRSF11B, IL23R, PDGFRA, CXCL13, EGF, and IL13, or a gene encoding the protein; a composition for diagnosing pancreatic cancer containing an agent capable of measuring the expression level of either at least one protein selected from the above-described group, or a gene encoding the protein; and a kit for diagnosing pancreatic cancer comprising the composition for diagnosing pancreatic cancer.

One embodiment of the present disclosure is directed to a biomarker composition for diagnosing pancreatic cancer containing at least one protein selected from the group consisting of CD27, fins-like tyrosine kinase 3 ligand (FLT3LG), and interleukin-7 receptor (IL-7R, IL7R), or a gene encoding the protein.

In the present disclosure, "CD27" belongs to the tumor necrosis factor receptor superfamily, and is associated with the development and long-term maintenance of T cell immunity. In the present disclosure, CD27 may be represented by SEQ ID NO: 1, but is not limited thereto.

In the present disclosure, the "fins-like tyrosine kinase 3 ligand (FLT3LG)" is encoded by the FLT3LG gene, and is a hematopoietic four helical bundle cytokine. It is structurally similar to stem cell factor (SCF) or colony stimulating factor 1 (CSF-1). In the present disclosure, the fms-like tyrosine kinase 3 ligand may be represented by SEQ ID NO: 2, but is not limited thereto.

In the present disclosure, the "interleukin-7 receptor (IL-7R (IL7R))" is expressed on the surfaces of naive and memory T cells, and consists of two subunits, interleukin-7 receptor-α (CD127) and common γ-chain receptor (CD132). In the present disclosure, the interleukin-7 receptor may be represented by SEQ ID NO: 3, but is not limited thereto.

In the present disclosure, the biomarker composition may further contain at least one protein selected from interleukin-32 (IL-32, IL32)) and interleukin-10RA (interleukin-10 receptor alpha, IL-10RA, IL10RA).

In one embodiment, the biomarker composition may be, for example, a combination of an interleukin-7 receptor (IL-7R) protein or a gene encoding the same, and an interleukin-10RA (IL-10RA) protein or a gene encoding the same. For example, the biomarker composition may be a combination of an interleukin-7 receptor (IL-7R) protein or a gene encoding the same, a fins-like tyrosine kinase 3 ligand (FLT3LG) protein or a gene encoding the same, and an interleukin-10RA (IL-10RA) protein or a gene encoding the same.

In the present disclosure, the biomarker composition is obtainable from a biological sample derived from a subject. The "biological sample" refers to any material, for example, a liquid biopsy, obtained or derived from a subject, and may be, for example, blood, serum or plasma. For example, the biological sample may be mononuclear cells, particularly, peripheral blood mononuclear cells (PBMCs), isolated from the blood, serum or plasma.

In the present disclosure, the "interleukin-32 (IL-32, IL32)" is a pro-inflammatory cytokine for inducing cells of the immune system to express inflammatory cytokines such as tumor necrosis factor-alpha (TNF-α) or interleukin-6. In the present disclosure, interleukin-32 may be represented by SEQ ID NO: 4, but is not limited thereto.

In the present disclosure, "interleukin-10 receptor alpha (IL-10RA, IL10RA)" is one of inflammatory cytokines and is known to be closely related to pain. In the present disclosure, sequence information on interleukin-10RA may be obtained from a previously published database such as www.ncbi.nlm.nih.gov/.

In the present disclosure, it is possible to measure the expression of CD27, fins-like tyrosine kinase 3 ligand (FLT3LG), or interleukin-7 receptor (IL-7R, IL7R) in a biological sample from a subject, that is, a subject who has or is likely to develop pancreatic cancer, for example, a liquid biopsy such as blood, serum or plasma, for example, mononuclear cells, particularly peripheral blood mononuclear cells (PBMCs), derived from the blood, serum or plasma.

In the present disclosure, the term "diagnosis" includes determining the susceptibility of a subject to a specific disease or disorder, or determining whether a subject currently is presently affected by a specific disease or disorder, or determining the prognosis of a subject affected by a specific disease or disorder (for example, identifying pre-metastatic or metastatic cancerous states, determining stages of cancer, or determining responsiveness of cancer to therapy), or therametrics (e.g., monitoring a subject's condition to provide information as to the efficacy of therapy). For the purposes of the present disclosure, the term "diagnosis" means determining whether pancreatic cancer has developed, the likelihood (risk) of developing pancreatic cancer, the stage or grade of pancreatic cancer, or the survival rate or responsiveness to therapy of a pancreatic cancer patient.

In the present disclosure, the "stage" refers to the extent of spread of cancer cells or the stage of cancer progression, and the international classification according to the progress of pancreatic cancer generally follows the TNM staging system. Here, 'T (Tumor Size)' is a classification according to the size of the primary tumor, 'N (Lymph Node)' is a classification according to the degree of lymph node metastasis, and 'M (Metastasis)' corresponds to a classification according to whether metastasis to other organs has occurred. The detailed classifications for T, N, and M are shown in Table 1 below, and the grades of pancreatic cancer based thereon are shown in Table 2 below.

TABLE 1

| TNM stage | | Definition |
|---|---|---|
| Size of the primary cancer (T-stage) | T0 | A tumor composed of tumor cells which are in the form of a malignant tumor, but are confined to the mucous membrane or epithelium and have not yet invaded the basement membrane. |
| | T1 | Lesions limited to the primary organ. A tumor which is mobile and has not invaded adjacent and surrounding tissues. |
| | T2 | A tumor having a size of about 2 to 5 cm. |
| | T3 | A tumor having a size greater than T2 but limited to the organs. |

TABLE 1-continued

| TNM stage | | Definition |
|---|---|---|
| | T4 | A tumor adhering to and invading the surrounding tissues. |
| Lymph node status | N0 | There is no evidence of lymph node involvement. |
| (N-stage) | N1 | A tumor that invades one lymph node (a size of 1 to 2 cm or more, usually up to 3 cm) which is palpable, mobile, and confined to the first position. |
| | N2 | A lymph node that is palpable, partially mobile, or hard. There is microscopic evidence of involvement, which is clinically intertwined and appears contralaterally or bilaterally (3 to 5 cm). |
| | N3 | A tumor which is completely fixed, is completely fixed to bones, large blood vessels, skin, nerves, etc., through passes through the capsule, and has a size of 6 cm or more. |
| Distant metastasis | M0 | No distant metastasis. |
| (M-stage) | M1 | Distant metastasis present. |

TABLE 2

| Stage classification | T1 | T2 | T3 | T4 |
|---|---|---|---|---|
| N0 | Stage 1 | | Stage 2 | |
| N1 | | Stage 3 | | |
| N2 | | | | |
| N3 | | | | |
| M1 | | Stage 4 | | |

In the present disclosure, the "grade of cancer" refers to the degree of maturity or differentiation of cancer cells, and can be classified into grade 1, grade 2 and grade 3 as shown in Table 3 below according to the degree of differentiation. Here, low grade cancer of grade 3 has problems of rapid metastasis, poor therapeutic effect, and poor prognosis after treatment, because the borders of the tumor are unclear compared to those in high grade or intermediate grade cancer of grade 2 or 1 (Histopathology. 2002 September; 41(3A):154-61, Nat Genet. 2008 May; 40(5):499-507, etc.).

TABLE 3

| Classification | Grade | Degree of differentiation |
|---|---|---|
| Grade 1 | High grade | Well differentiated |
| Grade 2 | Intermediate grade | Moderately differentiated |
| Grade 3 | Low grade | Poorly differentiated |

Another embodiment of the present disclosure is directed to a composition for diagnosing pancreatic cancer containing an agent for measuring the expression level of either at least one protein selected from the group consisting of CD27, fins-like tyrosine kinase 3 ligand (FLT3LG), and interleukin-7 receptor (IL7R), or a gene encoding the protein.

In the present disclosure, the composition for diagnosis of pancreatic cancer may further contain an agent for measuring the expression level of either at least one protein selected from interleukin-32 (IL-32) and interleukin-10RA (IL-10RA), or a gene encoding the protein.

In one embodiment, the composition for diagnosing pancreatic cancer may be, for example, a combination of an agent for measuring the expression level of an interleukin-7 receptor (IL-7R) protein or a gene encoding the same, and an agent for measuring the expression level of an interleukin-10RA (IL-10RA) protein or a gene encoding the same. For example, it may be a combination of an agent for measuring the expression level of an interleukin-7 receptor (IL-7R) protein or a gene encoding the same, an agent for measuring the expression level of a fins-like tyrosine kinase 3 ligand (FLT3LG) protein or a gene encoding the same, and an agent for measuring the expression level of an interleukin-10RA (IL-10RA) protein or a gene encoding the same.

In the present disclosure, the composition for diagnosing pancreatic cancer is applied to a biological sample derived from a subject. The "biological sample" refers to any material, for example, a liquid biopsy, obtained or derived from a subject, and may be, for example, blood, serum or plasma. For example, the biological sample may be mononuclear cells, particularly, peripheral blood mononuclear cells (PBMCs), isolated from the blood, serum or plasma.

In the present disclosure, the agent for measuring the expression level of CD27, fins-like tyrosine kinase 3 ligand (FLT3LG), interleukin-7 receptor (IL-7R), interleukin-10RA (IL-10RA) or interleukin-32 (IL-32) protein is not particularly limited, but may comprise, for example, at least one selected from the group consisting of an antibody, an oligopeptide, a ligand, a PNA (peptide nucleic acid) and an aptamer, which binds specifically to the protein.

In the present disclosure, the "antibody" refers to a substance that specifically binds to an antigen and causes an antigen-antibody reaction. For the purposes of the present disclosure, the antibody refers to an antibody that specifically binds to the biomarker protein. Examples of the antibody of the present disclosure include all of polyclonal antibodies, monoclonal antibodies, and recombinant antibodies. The antibody may be readily produced using techniques well known in the art. For example, the polyclonal antibody may be produced by a method well known in the art, which includes the process of obtaining a serum containing the antibody by injecting the antigen of the protein into an animal and collecting blood from the animal. This polyclonal antibody may be produced from any animal such as goat, rabbit, sheep, monkey, horse, pig, cow, dog, or the like. In addition, the monoclonal antibody may be produced using the hybridoma method well known in the art (see Kohler and Milstein (1976) European Journal of Immunology 6:511-519), or the phage antibody library technology (Clackson et al, Nature, 352:624-628, 1991; Marks et al, J. Mol. Biol., 222:58, 1-597, 1991). The antibody produced by the above method may be isolated and purified using a method such as gel electrophoresis, dialysis, salt precipitation, ion exchange chromatography, affinity chromatography, or the like. In addition, examples of the antibody of the present disclosure include not only a complete form having two full-length light chains and two full-length heavy chains, but also functional fragments of an antibody molecule. "Functional fragment of an antibody molecule" refers to a fragment having at least an antigen-binding function, and examples thereof include Fab, F(ab'), F(ab')2, Fv and the like.

In the present disclosure, "PNA (Peptide Nucleic Acid)" refers to an artificially synthesized DNA or RNA-like polymer, which was first introduced by the Professors Nielsen, Egholm, Berg and Buchardt at University of Copenhagen, Denmark in 1991. DNA has a phosphate-ribose sugar backbone, but PNA has repeated N-(2-aminoethyl)-glycine backbones linked via peptide bonds, and thus has a significantly increased binding affinity for DNA or RNA and significantly increased stability. Thus, PNA is used for molecular biology, diagnostic assays and antisense therapies. The PNA is disclosed in detail in the literature [Nielsen P E, Egholm M, Berg R H, Buchardt O (December 1991). "Sequence-selective recognition of DNA by strand displacement with a thymine-substituted polyamide". Science 254(5037): 1497-1500].

In the present disclosure, the "aptamer" refers to an oligonucleotide or a peptide molecule, and the general contents of the aptamer are disclosed in detail in the literature [Bock L C et al., Nature 355(6360):5646(1992); Hoppe-Seyler F, Butz K "Peptide aptamers: powerful new tools for molecular medicine". J Mol Med. 78(8):42630(2000); Cohen B A, Colas P, Brent R. "An artificial cell-cycle inhibitor isolated from a combinatorial library". Proc Natl Acad Sci USA. 95(24): 142727(1998)].

In the present disclosure, the agent for measuring the expression level of the gene encoding the CD27, fins-like tyrosine kinase 3 ligand (FLT3LG), interleukin-7 receptor (IL-7R), interleukin-10RA (IL-10RA) or interleukin-32 (IL-32) protein may comprise at least one selected from the group consisting of primers, probes, and antisense nucleotides, which bind specifically to the gene.

In the present disclosure, the term "primer" refers to a fragment that recognizes a target gene sequence, and comprises a pair of forward and reverse primers, but is preferably a pair of primers providing analysis results with specificity and sensitivity. When the nucleic acid sequence of the primer is a sequence inconsistent with the non-target sequence present in the sample, and thus is a primer that amplifies only the target gene sequence containing the complementary primer binding site without inducing non-specific amplification, high specificity may be imparted.

In the present disclosure, the term "probe" refers to a substance capable of binding specifically to a target substance to be detected in the sample, and refers to a substance capable of specifically detecting the presence of the target substance in the sample through the binding. The type of probe is not particularly limited so long as it is commonly used in the art. For example, the probe may be PNA (peptide nucleic acid), LNA (locked nucleic acid), a peptide, a polypeptide, a protein, an RNA or a DNA, for example PNA. More specifically, the probe is a biomolecule derived from an organism or an analogue thereof, or is produced in vitro. Examples of the probe include an enzyme, a protein, an antibody, a microorganism, an animal and/or plant cell and organ, a neuron, DNA and RNA. Examples of the DNA include cDNA, genomic DNA, and an oligonucleotide, examples of the RNA include genomic RNA, mRNA and an oligonucleotide, and examples of the protein include antibodies, antigens, enzymes, peptides, and the like.

In the present disclosure, the term "LNA (locked nucleic acid)" refers to a nucleic acid analogue containing a 2'-O or 4'-C methylene bridge [J Weiler, J Hunziker and J Hall Gene Therapy (2006) 13, 496.502]. LNA nucleosides comprise the common bases of DNA and RNA, and can form base pairs according to the Watson-Crick base-pair rule. However, LNA fails to form an ideal shape in the Watson-Crick bond due to "locking" of the molecule attributable to the methylene bridge. When LNA is incorporated in a DNA or RNA oligonucleotide, it can more rapidly pair with a complementary nucleotide chain, thus increasing the stability of the double strand.

In the present disclosure, the term "antisense" means an oligomer that has a nucleotide sequence and a backbone between subunits, wherein an antisense oligomer is hybridized with the target sequence in the RNA by Watson-Crick base pairing to typically allow the formation of RNA: oligomer heterodimers with the mRNA in the target sequence. The oligomer may have an accurate or approximate sequence complementarity to the target sequence.

Information on the CD27, fins-like tyrosine kinase 3 ligand (FLT3LG), interleukin-7 receptor (IL-7R), interleukin-10RA (IL-10RA) or interleukin-32 (IL-32) protein according to the present disclosure, or the gene encoding the protein is known. Thus, based on this information, any person skilled in the art will be able to easily design a primer, probe or antisense nucleotide that binds specifically to the gene encoding the protein.

In the present disclosure, it is possible to measure the expression level of either at least one protein selected from the group consisting of CD27, fins-like tyrosine kinase 3 ligand (FLT3LG), interleukin-7 receptor (IL-7R), interleukin-10RA (IL-10RA) and interleukin-32 (IL-32), or a gene encoding the same in a biological sample isolated from a subject, for example, a liquid biopsy such as blood, serum or plasma, for example, mononuclear cells, particularly peripheral blood mononuclear cells (PBMCs), derived from the blood, serum or plasma.

Another embodiment of the present disclosure is directed to a kit for diagnosing pancreatic cancer comprising the composition for diagnosing pancreatic cancer according to the present disclosure.

In the present disclosure, it is possible to predict the onset of pancreatic cancer or the likelihood of developing pancreatic cancer by using the diagnostic kit, and furthermore, it is possible to diagnose the course or prognosis of pancreatic cancer or the therapeutic effect against pancreatic cancer.

In the present disclosure, the kit may be an RT-PCR kit, a DNA chip kit, an ELISA kit, a protein chip kit, a rapid kit, or a multiple-reaction monitoring (MRM) kit, but is not limited thereto.

The kit for diagnosing pancreatic cancer according to the present disclosure may further comprise one or more other component compositions, solutions or devices suitable for the analysis method.

For example, the diagnostic kit according to the present disclosure may further comprise essential elements required for performing a reverse transcription polymerase chain reaction. The reverse transcription polymerase chain reaction kit comprises a primer pair specific for the gene encoding the marker protein. The primer is an oligonucleotide having a sequence specific for the nucleic acid sequence of the gene, and may have a length of about 7 bp to 50 bp, for example, about 10 bp to 30 bp. The kit may also comprise a primer specific for the nucleic acid sequence of the control gene. In addition, the reverse transcription polymerase chain reaction kit may comprise test tubes or other appropriate containers, reaction buffers (at various pHs and magnesium concentrations), deoxynucleotides (dNTPs), enzymes such as Taq-polymerase and reverse transcriptase, DNase and/or RNase inhibitors, DEPC water, sterile water, and the like.

In addition, the diagnostic kit of the present disclosure may comprise essential elements required for performing DNA chip assay. The DNA chip kit may comprise a substrate to which a cDNA or oligonucleotide corresponding to a gene or a fragment thereof is attached, and a reagent, an agent, an enzyme, and the like for producing a fluorescent-labeled probe. The substrate may also comprise a cDNA or oligonucleotide corresponding to a control gene or a fragment thereof.

In addition, the diagnostic kit of the present disclosure may comprise essential elements required for performing ELISA. The ELISA kit comprises an antibody specific for the protein. The antibody has high specificity and affinity for the marker protein and little cross-reactivity with other proteins, and is a monoclonal antibody, a polyclonal antibody or a recombinant antibody. The ELISA kit may also comprise an antibody specific for the control protein. In addition, the ELISA kit may comprise reagents capable of detecting the bound antibody, such as a labeled secondary antibody, chromophores, an enzyme (e.g., conjugated to an antibody) and substrates thereof, or other substances that may bind to the antibody.

Another embodiment of the present disclosure is directed to a method for providing information for diagnosing pancreatic cancer, the method comprising a step of measuring the expression level of either at least one protein selected from the group consisting of CD27, fins-like tyrosine kinase 3 ligand (FLT3LG), and interleukin-7 receptor (IL-7R), or a gene encoding the protein in a biological sample isolated from a subject.

In the present disclosure, the term “subject” refers to a subject whose onset of pancreatic cancer is uncertain and who is likely to develop pancreatic cancer.

In the present disclosure, the “biological sample” refers to any material, for example, a liquid biopsy, obtained or derived from a subject, and may be, for example, blood, serum or plasma. For example, the biological sample may be mononuclear cells, particularly, peripheral blood mononuclear cells (PBMCs), isolated from the blood, serum or plasma.

In conventional methods for measuring the expression level of a biomarker for diagnosis of pancreatic cancer, cells are isolated mainly from the tissue (for example, pancreatic tissue) predicted to a disease, and the expression level of the biomarker in the cells is measured. However, according to the present disclosure, it is possible to rapidly, simply and very accurately diagnose the onset of cancer, particularly pancreatic cancer, and the likelihood of developing the cancer, by measuring the expression level of the disease biomarker according to the present disclosure in a liquid biopsy isolated from the subject, for example, mononuclear cells, particularly peripheral blood mononuclear cells, contained in blood, serum or plasma.

In the present disclosure, the step of measuring the expression level may further comprise a step of measuring the expression level of either any one or more proteins selected from interleukin-32 (IL-32) and interleukin-10RA (IL-10RA), or a gene encoding the same.

In the present disclosure, the agent for measuring the expression level of the CD27, fins-like tyrosine kinase 3 ligand (FLT3LG), interleukin-7 receptor (IL-7R), interleukin-10RA (IL-10RA) or interleukin-32 (IL-32) protein is not particularly limited, but may comprise, for example, at least one selected from the group consisting of antibodies, oligopeptides, ligands, PNAs (peptide nucleic acids) and aptamers, which bind specifically to the biomarker protein.

In the present disclosure, methods for measuring or comparatively analyzing the expression level of the CD27, fins-like tyrosine kinase 3 ligand (FLT3LG), interleukin-7 receptor (IL-7R), interleukin-10RA (IL-10RA) or interleukin-32 (IL-32) protein include, but are not limited to, protein chip analysis, immunoassay, ligand-binding assay, MALDI-TOF (matrix-assisted laser desorption/ionization time of flight mass spectrometry) analysis, SELDI-TOF (surface enhanced laser desorption/ionization-time of flight mass spectrometry) assay, radiation immunoassay, radiation immunodiffusion, Ouchterlony immunodiffusion, rocket immunoelectrophoresis, tissue immunostaining, complement fixation assay, 2D electrophoresis assay, liquid chromatography-mass spectrometry (LC-MS), liquid chromatography-mass spectrometry/mass spectrometry (LC-MS/MS), Western blotting, enzyme-linked immunosorbent assay (ELISA), and the like.

In the present disclosure, the agent for measuring the expression level of the gene encoding the CD27, fins-like tyrosine kinase 3 ligand (FLT3LG), interleukin-7 receptor (IL-7R), interleukin-10RA (IL-10RA) or interleukin-32 (IL-32) protein may comprise at least one selected from the group consisting of primers, probes and antisense oligonucleotides, which bind specifically to the gene encoding the protein.

In the present disclosure, the analysis method of measuring the expression level of the gene encoding the CD27, fins-like tyrosine kinase 3 ligand (FLT3LG), interleukin-7 receptor (IL-7R), interleukin-10RA (IL-10RA) or interleukin-32 (IL-32) protein to confirm the presence or expression level of the gene may be performed using, but not limited to, reverse transcription polymerase chain reaction (RT-PCR), competitive reverse transcription polymerase chain reaction (competitive RT-PCR), real-time RT-PCR, RNase protection assay (RPA), Northern blotting, DNA chip assay, or the like.

The method of the present disclosure may further comprise a step of determining that pancreatic cancer has occurred or predicting that the likelihood of developing pancreatic cancer is high, when the expression level of either at least one protein selected from the group consisting of CD27, fins-like tyrosine kinase 3 ligand (FLT3LG), and interleukin-7 receptor (IL-7R), or the gene encoding the protein, measured in the biological sample from the subject, is higher than the expression level in the normal control group.

In addition, the method of the present disclosure may comprise a step of determining that pancreatic cancer has occurred or predicting that the likelihood of developing pancreatic cancer is high, when the expression level of either at least one protein selected from among interleukin-32 (IL-32) and interleukin-10RA (IL-10RA), or the gene encoding the protein, measured in the biological sample from the subject, is higher than the expression level in the normal control group. When the measured expression level of the protein or the gene encoding the same is 1.2- to 20-fold higher, for example, 1.2-fold higher, 2-fold higher, 3-fold higher, 4-fold higher, 5-fold higher, 6-fold higher, 7-fold higher, or 8-fold higher than the expression level in the normal control group, it may be predicted that the likelihood of developing pancreatic cancer is high.

In addition, the method of the present disclosure may further comprise a step of predicting the likelihood of developing pancreatic cancer by substituting the expression levels of CD27, fins-like tyrosine kinase 3 ligand (FLT3LG), and interleukin-7 receptor (IL-7R), measured in the biological sample from the subject, into the following Equation 1 to obtain an LP value, and substituting the LP value into the following Equation 2:

$$LP = A - B \times (IL-7R) - C \times (FLT3LG) - D \times (CD27) \quad \text{[Equation 1]}$$

$$\text{Probability of developing pancreatic cancer} = 1/(1+\exp(-LP)) \quad \text{[Equation 2]}$$

In Equation 1 above,

A is a value of 3 to 4; B is a value of 0.5 to 1.5; C is a value of 0.1 to 0.7; and D is a value greater than 0 and not greater than 0.4, IL-7R may be the expression level value of the IL-7R protein or the gene encoding the same relative to a housekeeping protein or gene, measured in the biological sample from the subject; FLT3LG may be the expression level value of the FLT3LG protein or the gene encoding the same relative to the housekeeping protein or gene, measured in the biological sample from the subject; and CD27 may be the expression level value of the CD27 protein or the gene encoding the same relative to the housekeeping protein or gene, measured in the biological sample from the subject.

In the present disclosure, A in Equation 1 above may be a value of 3 to 4, for example, a value of 3.5 to 4, for example, a value of 3.7 to 4.0, for example, 3.8688.

In the present disclosure, B in Equation 1 above may be a value of 0.5 to 1.5, for example, a value of 0.8 to 1.3, for example, a value of 0.9 to 1.1, for example, 1.0342.

In the present disclosure, C in Equation 1 above may be a value of 0.1 to 0.7, for example, a value of 0.1 to 0.5, for example, a value of 0.2 to 0.4, for example, 0.3365.

In the present disclosure, D in Equation 1 above may be a value of greater than 0 and not greater than 0.4, for example, a value of 0.01 to 0.3, for example, a value of 0.02 to 0.1, for example, 0.0526.

In the present disclosure, IL-7R in Equation 1 above may be a ΔCt value which is the expression level value of the IL-7R protein or the gene encoding the same relative to a normalization housekeeping protein or gene, measured in the biological sample from the subject.

In the present disclosure, FLT3LG in Equation 1 above may be a ΔCt value which is the expression level value of the FLT3LG protein or the gene encoding the same relative to the normalization housekeeping protein or gene, measured in the biological sample from the subject.

In the present disclosure, CD27 in Equation 1 above may be a ΔCt value which is the expression level value of the CD27 protein or the gene encoding the same relative to the normalization housekeeping protein or gene, measured in the biological sample from the subject.

Here, the normalization housekeeping protein or gene may be glyceraldehyde-3-phosphate dehydrogenase (GAPDH), Cyclophilin I (CypI), albumin, actin, tubulin, cyclophilin hypoxantine phosphoribosyltransferase (HPRT), L32, 28S, 18S, or the like, but is not limited thereto.

In the present disclosure, the probability of developing pancreatic cancer may be predicted or determined by substituting the LP value, obtained from Equation 1, into Equation 2.

In the present disclosure, the value obtained from Equation 2 may be 0 to 1, and it may be predicted that the closer to 1, the higher the likelihood of developing pancreatic cancer.

In addition, when the value obtained from Equation 2 is 0.5 to 1, 0.55 to 1, 0.6 to 1, 0.65 to 1, 0.7 to 1, 0.75 to 1, 0.8 to 1, 0.85 to 1, 0.9 to 1, or 0.95 or 1, it may be predicted that the likelihood of developing pancreatic cancer is high or determined that pancreatic cancer has developed.

Furthermore, the method of the present disclosure may further comprise a step of subjecting the subject to appropriate treatment such as administration of a drug for the disease (such as an anticancer drug for pancreatic cancer), gene therapy, radiotherapy or immunotherapy, when the likelihood of developing pancreatic cancer is predicted or diagnosed to be high as a result of measuring the expression level of at least one protein selected from the group consisting of CD27, fins-like tyrosine kinase 3 ligand (FLT3LG), and interleukin-7 receptor (IL-7R) or the gene encoding the protein, measured in the biological sample from the subject.

Another embodiment of the present disclosure is directed to an apparatus for diagnosing pancreatic cancer comprising a diagnosis unit configured to determine information for pancreatic cancer diagnosis from data including the expression level of either at least one protein selected from the group consisting of CD27, fins-like tyrosine kinase 3 ligand (FLT3LG), and interleukin-7 receptor (IL-7R), or a gene encoding the protein, measured in a biological sample isolated from a subject.

FIG. 1 schematically illustrates the structure of an apparatus for diagnosing pancreatic cancer according to one embodiment of the present disclosure.

The apparatus for diagnosing pancreatic cancer according to the present disclosure may further comprise a sample receiving unit 100 configured to receive the biological sample isolated from the subject.

In the present disclosure, the "biological sample" refers to any material, for example, a liquid biopsy, obtained or derived from the subject, and may be, for example, blood, serum or plasma. For example, the biological sample may be mononuclear cells, particularly, peripheral blood mononuclear cells (PBMCs), isolated from the blood, serum or plasma.

The apparatus for diagnosing pancreatic cancer according to the present disclosure may further comprise an input unit 200 configured to input the expression level (diagnosis target data) of either at least one protein selected from the group consisting of CD27, fins-like tyrosine kinase 3 ligand (FLT3LG), and interleukin-7 receptor (IL-7R), or a gene encoding the protein, measured in the biological sample received in the sample receiving unit. In the present disclosure, the diagnosis target data, for example, a ΔCt value which is the expression level value of either at least one protein selected from the group consisting of CD27, fins-like tyrosine kinase 3 ligand (FLT3LG), and interleukin-7 receptor (IL-7R), or the gene encoding the protein, relative to a normalization housekeeping protein or gene, measured in the biological sample isolated from the subject, may be input into the input unit 200.

In addition, in the present disclosure, pre-processing such as alignment, normalization, and/or scaling for the diagnosis target data may be performed in the input unit 200, or the diagnosis target data that has been pre-processed may be input into the input unit.

In the present disclosure, multiple diagnosis target data for one subject may also be input into the input unit 200.

In the input unit 200, particularly, of the apparatus for diagnosing pancreatic cancer according to the present disclosure, details regarding the agent and the method for measuring the expression level of either at least one protein selected from the group consisting of CD27, fins-like tyrosine kinase 3 ligand (FLT3LG), and interleukin-7 receptor (IL-7R), or the gene encoding the protein overlap with those described in the method for providing information for diagnosing pancreatic cancer, and thus detailed description thereof will be omitted to avoid excessive complexity of the specification.

The apparatus for diagnosing pancreatic cancer according to the present disclosure may comprise a diagnosis unit 300 configured to determine pancreatic cancer diagnosis information based on the diagnosis target data input from the input unit 200.

In the present disclosure, the diagnosis unit 300 may determine whether the biological sample is positive or negative for pancreatic cancer, based on the likelihood of developing pancreatic cancer or whether pancreatic cancer has occurred, determined based on the diagnosis target data.

In the present disclosure, the diagnosis unit 300 may determine that the likelihood of developing pancreatic cancer is high or the biological sample is positive for pancreatic cancer, when the expression level of either at least one protein selected from the group consisting of CD27, fins-like tyrosine kinase 3 ligand (FLT3LG), and interleukin-7 receptor (IL-7R), or the gene encoding the protein, which is measured in the biological sample isolated from the subject and is the diagnosis target data input from the input unit 200, is higher than that in the normal control group.

In the present disclosure, the diagnosis unit 300 may determine the probability of developing pancreatic cancer by substituting the expression levels of CD27, fins-like tyrosine kinase 3 ligand (FLT3LG), and interleukin-7 receptor (IL-7R), which are the diagnosis target data input into the input unit 200, measured in the biological sample from the subject, into the following Equation 1 to obtain an LP value, and substituting the LP value into the following Equation 2:

$$LP = A - B \times (IL-7R) - C \times (FLT3LG) - D \times (CD27) \quad \text{[Equation 1]}$$

$$\text{Probability of developing pancreatic cancer} = 1/(1+\exp(-LP)) \quad \text{[Equation 2]}$$

In Equation 1 above,

A is a value of 3 to 4; B is a value of 0.5 to 1.5; C is a value of 0.1 to 0.7; and D is a value greater than 0 and not greater than 0.4, IL-7R may be the expression level value of the IL-7R protein or the gene encoding the same relative to a housekeeping protein or gene, measured in the biological sample from the subject; FLT3LG may be the expression level value of the FLT3LG protein or the gene encoding the same relative to the housekeeping protein or gene, measured in the biological sample from the subject; and CD27 may be the expression level value of the CD27 protein or the gene encoding the same relative to the housekeeping protein or gene, measured in the biological sample from the subject.

In the present disclosure, A in Equation 1 above may be a value of 3 to 4, for example, a value of 3.5 to 4, for example, a value of 3.7 to 4.0, for example, 3.8688.

In the present disclosure, B in Equation 1 above may be a value of 0.5 to 1.5, for example, a value of 0.8 to 1.3, for example, a value of 0.9 to 1.1, for example, 1.0342.

In the present disclosure, C in Equation 1 above may be a value of 0.1 to 0.7, for example, a value of 0.1 to 0.5, for example, a value of 0.2 to 0.4, for example, 0.3365.

In the present disclosure, D in Equation 1 above may be a value of greater than 0 and not greater than 0.4, for example, a value of 0.01 to 0.3, for example, a value of 0.02 to 0.1, for example, 0.0526.

In the present disclosure, IL-7R in Equation 1 above may be a ΔCt value which is the expression level value of the IL-7R protein or the gene encoding the same relative to a normalization housekeeping protein or gene, measured in the biological sample from the subject.

In the present disclosure, FLT3LG in Equation 1 above may be a ΔCt value which is the expression level value of the FLT3LG protein or the gene encoding the same relative to the normalization housekeeping protein or gene, measured in the biological sample from the subject.

In the present disclosure, CD27 in Equation 1 above may be a ΔCt value which is the expression level value of the CD27 protein or the gene encoding the same relative to the normalization housekeeping protein or gene, measured in the biological sample from the subject.

Here, the normalization housekeeping protein or gene may be glyceraldehyde-3-phosphate dehydrogenase (GAPDH), Cyclophilin I (CypI), albumin, actin, tubulin, cyclophilin hypoxantine phosphoribosyltransferase (HPRT), L32, 28S, 18S, or the like, but is not limited thereto.

In the present disclosure, the probability of developing pancreatic cancer may be predicted or determined by substituting the LP value, obtained from Equation 1, into Equation 2. In the present disclosure, the value obtained from Equation 2 may be 0 to 1, and it may be determined that the closer to 1, the higher the likelihood of developing pancreatic cancer.

In addition, when the value obtained from Equation 2 is 0.5 to 1, 0.55 to 1, 0.6 to 1, 0.65 to 1, 0.7 to 1, 0.75 to 1, 0.8 to 1, 0.85 to 1, 0.9 to 1, or 0.95 or 1, it may be predicted that the likelihood of developing pancreatic cancer is high or determined that the biological sample is positive for pancreatic cancer.

The apparatus for diagnosing pancreatic cancer according to the present disclosure may further comprise an output unit 400 configured to output the diagnosis result obtained by the diagnosis unit 300.

In the present disclosure, the output unit 400 may be composed of an output means such as a display or a speaker, but is not limited thereto.

In the present disclosure, the apparatus for diagnosing pancreatic cancer may be performed on a computer system.

Another embodiment of the present disclosure is directed to a method for screening a drug for inducing pancreatic cancer, the method comprising steps of: treating an isolated biological sample with a candidate substance expected to induce pancreatic cancer; and measuring the expression level of either at least one protein selected from the group consisting of CD27, fins-like tyrosine kinase 3 ligand (FLT3LG), and interleukin-7 receptor (IL-7R), or a gene encoding the protein, in the biological sample treated with the candidate substance.

In the present disclosure, the isolated biological sample may be a biological sample isolated from a subject with or without pancreatic cancer. Specifically, the biological sample refers to any material, for example, a liquid biopsy, obtained or derived from a subject, and may be, for example, blood, serum or plasma. For example, the biological sample may be mononuclear cells, particularly, peripheral blood mononuclear cells (PBMCs), isolated from the blood, serum or plasma.

In addition, in the present disclosure, the candidate substance comprises any substance, molecule, element, compound, entity, or a combination thereof. Examples of the candidate substance include, but are not limited to, proteins, polypeptides, small organic molecules, polysaccharides, polynucleotides, and the like. In addition, the candidate substance may also be a natural product, a synthetic compound, or a combination of two or more substances.

In the present disclosure, the step of measuring the expression level further comprise a step of measuring the expression level of either any one or more proteins selected from among interleukin-32 (IL-32) protein and interleukin-10RA (IL-10RA), or a gene encoding the same.

In the present disclosure, the method may further comprise a step of determining that the candidate substance is an inducer of pancreatic cancer, when the expression level of either at least one protein selected from the group consisting of CD27, fins-like tyrosine kinase 3 ligand (FLT3LG), and interleukin-7 receptor (IL-7R), or a gene encoding the protein, in the biological sample after treatment with the candidate substance, is higher than that before treatment with the candidate substance.

In addition, in the present disclosure, the method may further comprise a step of determining that the candidate substance is an inducer of pancreatic cancer, when the expression level of either at least one protein selected from among interleukin-32 (IL-32) protein and interleukin-10RA (IL-10RA), or the gene encoding the same, in the biological sample after treatment with the candidate substance, is higher than that before treatment with the candidate substance.

In the present disclosure, details regarding the method for measuring the expression level of the biomarker protein or the gene encoding the protein, and pancreatic cancer and diagnosis thereof overlap with those described in the method for providing information for diagnosing pancreatic cancer, and thus description thereof will be herein omitted to avoid excessive complexity of the specification.

Another embodiment of the present disclosure is directed to a pharmaceutical composition for preventing or treating pancreatic cancer containing, as an active ingredient, an agent for inhibiting the expression or activity of interleukin-10 receptor beta (IL-10RB, IL10RB).

The term "interleukin-10RB" as used herein may be used interchangeably with term "IL-10RB", "IL10RB", "IL-10R2", or "IL10R2".

As used herein, the term "preventing" may refer to any action that inhibits pancreatic cancer or delays the development of pancreatic cancer by administering the pharmaceutical composition of the present disclosure.

As used herein, the term "treating" may refer to any action that alleviates or beneficially changes symptoms of pancreatic cancer by administering the pharmaceutical composition of the present disclosure.

In the present disclosure, the agent for inhibiting the expression may be an antisense oligonucleotide, siRNA, shRNA, miRNA, or a vector containing the same, against the gene encoding the interleukin-10RB protein. This antisense oligonucleotide, siRNA, shRNA, miRNA, or vector containing the same may be constructed using a method known in the art. As used herein, the term "vector" refers to a genetic construct containing an external DNA inserted into a genome encoding a polypeptide. The vector related to the present disclosure is a vector in which a nucleic acid sequence inhibiting the gene is inserted into a genome. Examples of the vector include a DNA vector, a plasmid vector, a cosmid vector, a bacteriophage vector, a yeast vector, or a viral vector.

In addition, in the present disclosure, the agent for inhibiting the activity refers to a substance that decreases the function of the interleukin-10RB protein. Preferably, it refers to a substance that makes the protein present at a level at which the function of the protein is not detectable or is insignificant. More specifically, the agent for inhibiting the activity may be either an antibody that binds specifically to the interleukin-10RB protein, or an antisense oligonucleotide, siRNA, shRNA, miRNA, or vector including the same, against a gene encoding a specific fragment in the interleukin-10RB protein, but is not limited thereto.

In one embodiment, the agent for inhibiting the expression or activity of interleukin-10RB may be, for example, a substance that binds specifically to the IL-10RB protein or mRNA encoding the protein. For example, this agent may be a primer, probe, an oligonucleotide, an antibody or an antigen-binding fragment thereof, a ligand, a receptor, an agonist or an antagonist, or a combination thereof, which binds specifically to the IL-10RB protein or the mRNA encoding the protein.

In one embodiment, the composition may inhibit the expression or activity of IL-10RB in peripheral blood mononuclear cells (PBMCs).

In one embodiment, the composition may reduce the growth or proliferation of pancreatic cancer cells or activate lymph nodes around pancreatic cancer cells.

The pharmaceutical composition is administered in a pharmaceutically effective amount. The term "pharmaceutically effective amount" refers to an amount sufficient to treat a disease at a reasonable benefit/risk ratio applicable to any medical treatment. The effective dose level of the pharmaceutical composition may be determined depending on factors, including the patient's disease type, the severity of the disease, the activity of the drug, sensitivity to the drug, the time of administration, the route of administration, excretion rate, the duration of treatment, and factors including drugs used simultaneously with the composition, as well as other factors well known in the medical field. The pharmaceutical composition of the present disclosure may be administered individually or in combination with other therapeutic agents, and may be administered sequentially or simultaneously with conventional therapeutic agents. The pharmaceutical composition may be administered in a single or multiple dosage form. It is important to administer the pharmaceutical composition in the minimum amount that may exhibit the maximum effect without causing side effects, in view of all the above-described factors, and this amount may be easily determined by a person skilled in the art.

Specifically, the effective amount of the pharmaceutical composition of the present disclosure may vary depending on the patient's age, sex, condition and body weight, the absorption rate of the active ingredient in vivo, inactivation rate, excretion rate, the type of disease, and drugs used in combination. Generally, the pharmaceutical composition may be administered daily or every other day at a dose of 0.01 to 500 mg/kg body weight, or may be administered 1 to 5 times a day at this dose. However, the dose is not intended to limit the scope of the present disclosure in any way, because the dose may increase or decrease depending on the route of administration, the severity of obesity, the patient's sex, weight and age, etc.

In another aspect of the present disclosure, the present disclosure provides a method for treating pancreatic cancer, the method comprising a step of administering the pharmaceutical composition to a subject. As used herein, the term "subject" means a subject in need of treatment of the disease, and more specifically, means mammals, including human or non-human primates, mice, dogs, cats, horses, and cows.

Advantageous Effects

According to the composition or method according to the present disclosure, it is possible to diagnose pancreatic cancer simply and quickly and very accurately in a non-invasive manner, unlike a conventional art.

In addition, the composition or method according to the present disclosure enables early diagnosis of pancreatic cancer, and thus may be used for appropriate diagnosis and treatment of a precancerous lesion of pancreatic cancer.

BRIEF DESCRIPTION OF DRAWINGS

FIG. 1 schematically illustrates the structure of an apparatus for diagnosing pancreatic cancer according to one embodiment of the present disclosure.

FIG. 2 graphically shows the results of comparing the expression levels of IL-7R in peripheral blood mononuclear cells derived from a normal control group and pancreatic cancer patients, in one example of the present disclosure.

FIG. 3 graphically shows the results of comparing the expression levels of IL-32 in peripheral blood mononuclear cells derived from a normal control group and pancreatic cancer patients, in one example of the present disclosure.

FIG. 4 graphically shows the results of comparing the expression levels of FLT3LG in peripheral blood mononuclear cells derived from a normal control group and pancreatic cancer patients, in one example of the present disclosure.

FIG. 5 graphically shows the results of comparing the expression levels of IL-10RA in peripheral blood mononuclear cells derived from a normal control group and pancreatic cancer patients, in one example of the present disclosure.

FIG. 6 shows ROC curve analysis for an IL-7R biomarker in pancreatic cancer diagnosis, in one example of the present disclosure.

FIG. 7 shows ROC curve analysis for an IL-32 biomarker in pancreatic cancer diagnosis, in one example of the present disclosure.

FIG. 8 shows ROC curve analysis for a FLT3LG biomarker in pancreatic cancer diagnosis, in one example of the present disclosure.

FIG. 9 shows ROC curve analysis for an IL-10RA biomarker in pancreatic cancer diagnosis, in one example of the present disclosure.

FIG. 10 graphically shows the results of comparing the expression levels of IL-7R in peripheral blood mononuclear cells derived from a normal control group and pancreatic cancer patients, in one example of the present disclosure.

FIG. 11 graphically shows the results of comparing the expression levels of FLT3LG in peripheral blood mononuclear cells derived from a normal control group and pancreatic cancer patients, in one example of the present disclosure.

FIG. 12 graphically shows the results of comparing the expression levels of CD27 in peripheral blood mononuclear cells derived from a normal control group and pancreatic cancer patients, in one example of the present disclosure.

FIG. 13 shows ROC curve analysis for an IL-7R biomarker in pancreatic cancer diagnosis, in one example of the present disclosure.

FIG. 14 shows ROC curve analysis for a FLT3LG biomarker in pancreatic cancer diagnosis, in one example of the present disclosure.

FIG. 15 shows ROC curve analysis for a CD27 biomarker in pancreatic cancer diagnosis, in one example of the present disclosure.

FIG. 16 schematically illustrates a process of evaluating the efficacy of a pancreatic cancer-specific biomarker using a pancreatic cancer animal model according to one embodiment of the present disclosure.

FIG. 17 shows time-dependent changes in the weights of tumor tissue and spleen in the pancreatic cancer animal model of the present disclosure.

FIG. 18 shows time-dependent changes in the expression levels of IL-7R, IL-22R1 or IL-10RB in peripheral blood mononuclear cells derived from a normal control group and pancreatic cancer animal model, in one example of the present disclosure.

FIG. 19 is a graph showing the results of analyzing the proliferation level of pancreatic cancer cells by CCK-8 assay on day 1 of culture after inoculating a pancreatic cancer cell culture with IL-10RB$^+$ PBMC conditioned medium (CM), in comparison with the case in which the pancreatic cancer cell culture was inoculated with IL-10RB$^-$ PBMC conditioned medium (CM).

FIG. 20 is a graph showing the results of analyzing the proliferation level of pancreatic cancer cells by CCK-8 assay on day 2 of culture after inoculating a pancreatic cancer cell culture with IL-10RB$^+$ PBMC conditioned medium (CM), in comparison with the case in which the pancreatic cancer cell culture was inoculated with IL-10RB$^-$ PBMC conditioned medium (CM).

FIG. 21 is a graph showing the results of analyzing the proliferation level of pancreatic cancer cells by CCK-8 assay on day 3 of culture after inoculating a pancreatic cancer cell culture with IL-10RB$^+$ PBMC conditioned medium (CM), in comparison with the case in which the pancreatic cancer cell culture was inoculated with IL-10RB$^-$ PBMC conditioned medium (CM).

FIG. 22 is a graph showing the results of analyzing the proliferation level of pancreatic cancer cells by FACS analysis on day 2 of culture after inoculating a pancreatic cancer cell culture with IL-10RB$^+$ PBMC conditioned medium (CM), in comparison with the case in which the pancreatic cancer cell culture was inoculated with IL-10RB$^-$ PBMC conditioned medium (CM).

FIG. 23 is a graph showing the results of analyzing the proliferation level of pancreatic cancer cells by FACS analysis on day 3 of culture after inoculating a pancreatic cancer cell culture with IL-10RB$^+$ PBMC conditioned medium (CM), in comparison with the case in which the pancreatic cancer cell culture was inoculated with IL-10RB$^-$ PBMC conditioned medium (CM).

FIG. 24 is a graph showing the results of analyzing the proliferation level of pancreatic cancer cells by CCK-8 assay on day 1 of culture after inoculating a pancreatic cancer cell culture with IL-10RB$^+$ PBMC conditioned medium (CM) or IL-10RB$^-$ PBMC conditioned medium (CM) and additionally inoculating some experimental groups with anti-IL-10RB normalizing antibody (R&D).

FIG. 25 is a graph showing the results of analyzing the proliferation level of pancreatic cancer cells by CCK-8 assay on day 1 of culture after inoculating a pancreatic cancer cell culture with IL-10RB$^+$ PBMC conditioned medium (CM) or IL-10RB$^-$ PBMC conditioned medium (CM) and additionally inoculating some experimental groups with anti-IL-10RB normalizing antibody (Novus).

FIG. 26 is a graph showing the results of analyzing the proliferation level of pancreatic cancer cells by CCK-8 assay on day 2 of culture after inoculating a pancreatic cancer cell culture with IL-10RB$^+$ PBMC conditioned medium (CM) or IL-10RB$^-$ PBMC conditioned medium (CM) and additionally inoculating some experimental groups with anti-IL-10RB normalizing antibody (R&D).

FIG. 27 is a graph showing the results of analyzing the proliferation level of pancreatic cancer cells by CCK-8 assay on day 2 of culture after inoculating a pancreatic cancer cell culture with IL-10RB$^+$ PBMC conditioned medium (CM) or IL-10RB$^-$ PBMC conditioned medium (CM) and additionally inoculating some experimental groups with anti-IL-10RB normalizing antibody (Novus).

FIG. 28 is a graph showing the results of analyzing the proliferation level of pancreatic cancer cells by CCK-8 assay on day 3 of culture after inoculating a pancreatic cancer cell culture with IL-10RB$^+$ PBMC conditioned medium (CM) or IL-10RB$^-$ PBMC conditioned medium (CM) and additionally inoculating some experimental groups with anti-IL-10RB normalizing antibody (R&D).

FIG. 29 is a graph showing the results of analyzing the proliferation level of pancreatic cancer cells by CCK-8 assay on day 3 of culture after inoculating a pancreatic cancer cell culture with IL-10RB$^+$ PBMC conditioned medium (CM) or IL-10RB$^-$ PBMC conditioned medium (CM) and additionally inoculating some experimental groups with anti-IL-10RB normalizing antibody (Novus).

FIG. 30 is a graph showing the results of analyzing the proliferation level of pancreatic cancer cells by FACS analysis on day 2 of culture after inoculating a pancreatic cancer cell culture with IL-10RB$^+$ PBMC conditioned medium (CM) or IL-10RB$^-$ PBMC conditioned medium (CM) and additionally inoculating some experimental groups with anti-IL-10RB normalizing antibody (R&D).

FIG. 31 is a graph showing the results of analyzing the proliferation level of pancreatic cancer cells by FACS analysis on day 2 of culture after inoculating a pancreatic cancer cell culture with IL-10RB$^+$ PBMC conditioned medium (CM) or IL-10RB$^-$ PBMC conditioned medium (CM) and additionally inoculating some experimental groups with anti-IL-10RB normalizing antibody (Novus).

FIG. 32 is a graph showing the results of analyzing the proliferation level of pancreatic cancer cells by FACS analysis on day 3 of culture after inoculating a pancreatic cancer cell culture with IL-10RB$^+$ PBMC conditioned medium (CM) or IL-10RB$^-$ PBMC conditioned medium (CM) and additionally inoculating some experimental groups with anti-IL-10RB normalizing antibody (R&D).

FIG. 33 is a graph showing the results of analyzing the proliferation level of pancreatic cancer cells by FACS analysis on day 3 of culture after inoculating a pancreatic cancer cell culture with IL-10RB$^+$ PBMC conditioned medium (CM) or IL-10RB$^-$ PBMC conditioned medium (CM) and additionally inoculating some experimental groups with anti-IL-10RB normalizing antibody (Novus).

FIG. 34 is a graph showing the results of analyzing changes in the expression level of IL-10RB in PBMCs isolated from IL-22 KO mice.

FIG. 35 is a graph showing the results of analyzing changes in the expression level of IL-10RB in PBMCs that invaded pancreatic cancer cells isolated from IL-22 KO mice.

FIG. 36 shows FACS analysis results obtained by comparing the number of IL-10RB$^+$ PBMCs among CD11b-stained cells between PBMCs isolated from IL-22 KO mice and PBMCs isolated from B6 mice (WT).

FIG. 37 shows FACS analysis results obtained by comparing the number of IL-10RB$^+$ PBMCs among CD11b-stained cells between PBMCs isolated from IL-22 KO mice and B6 mice (WT) after injection of pancreatic cancer cells into the mice.

FIG. 38 depicts images showing changes in the size of pancreatic cells obtained from IL-22 KO mice and B6 mice (WT) after injection of pancreatic cancer cells into the mice.

FIG. 39 is a graph showing changes in the weight (g) of pancreatic cells obtained from IL-22 KO mice and B6 mice (WT) after injection of pancreatic cancer cells into the mice.

FIG. 40 is a graph showing changes in the size of lymph nodes around pancreatic cancer cells after injection of pancreatic cancer cells into IL-22 KO mice and B6 mice (WT).

FIG. 41 depicts images showing the state of lymph nodes, which may determine the degree of recovery of lymph glands around pancreatic cancer cells after injection of pancreatic cancer cells into IL-22 KO mice and B6 mice (WT).

FIG. 42 is a graph showing the results of analyzing the proliferation level of pancreatic cancer cells when inhibiting IL-10RB (IL10RB), IL-22R1, TNF-α, IFN-γ, IL-2, IL-6 or IL-22 protein.

MODE FOR INVENTION

Hereinafter, the present disclosure will be described in more detail with reference to examples. It will be obvious to those skilled in the art that these examples serve merely to illustrate the present disclosure, and the scope of the present disclosure is not limited by these examples.

EXAMPLES

[Experimental Example 1] Identification of Pancreatic Cancer-Specific Biomarkers (1)

1. scRNA-seq Experiment

IL-10RB$^+$ cells were enriched from peripheral blood mononuclear cells (PBMCs) of Pancreatic Ductal Adeno Carcinoma (PDAC) patients using a FACS Aria III flow cytometer (BD Biosciences). In order to count the number of cells and determine the cell death rate, the isolated cells were stained with trypan blue and diluted to a concentration of $1\times10^5$ to $2\times10^6$ cells/ml. The cell death rate was estimated to be about 90%. A scRNA-seq library was formed using the Chromium system (10× Genomics) together with the Chromium Single Cell 3' Library & Gel Bead Kit v2. The cell suspension was loaded on a Chromium Single Cell A Chip to capture 5,000 to 6,000 cells per channel. Cell lysis and reverse transcription were performed in gel bead-in-emulsions (GEMs) using a C1000 Touch Thermal Cycler (Bio-Rad). Next, cDNA amplification and library preparation were performed, and sequencing libraries were pooled for multiplexing, and then sequenced on a NovaSeq 6000 platform (Illumina).

2. scRNA-seq Data Analysis

The raw FASTQ file was processed by Cell Ranger software suite (v2.2.0) with default mapping options. Reads were mapped to the human reference genome (GRCh38) using STAR (v2.5.1b), and then quantified with the Ensembl GTF file (release 91). Cell barcodes associated with empty droplets were removed from the gene-by-cell count matrix using the emptyDrops function of the DropletUtils (v1.2.2) R package with FDR<0.01. To filter out low-quality cells, cells with 10% or more of unique molecular identifiers (UMIs) assigned to mitochondrial genes, or with not more than 1,000 total UMIs or with 10 or less expressed genes were excluded. The thresholds were determined by visually inspecting outliers in 2D principal component analysis on all the quality control metrics calculated using the calculateQCMetrics function of the scater (v1.10.1) R package. Using the NormalizeData function of the Seurat (v3.0-alpha) package R, each calculated value was divided by the total calculated value of each cell, multiplied by a 10,000 scale value, and then log-transformed with a pseudo-count of 1. From each data, the most variable top 2,000 genes were selected as a subset of feature genes using the FindVariableFeatures function of the Seurat package with default options. From 3D canonical correlation vectors, a batch effect was removed using the FindIntegrationAnchors and IntegrateData functions of the Seurat package. The integrated expression matrix was scaled using the ScaleData function of the Seurat package, and then cells were visualized in the two-dimensional UMAP plot using the RunUMAP function of the Seurat package on 30 principal components. For cell type annotation, the CreateSinglerSeuratObject function of the SingleR package (v.0.2.2) R was used in the raw UMI coefficient matrix, and the following parameters were set: npca=15, min.cells=0, min.genes=0, and regress.out=NULL. Genes or cell type marker genes that are differentially expressed between P5 and P5(−) were identified using the Wilcoxon rank sum test provided in the Seurat package with an option of adjusted P-value<0.01.

3. Analysis Results

Through the above analysis, biomarkers that are significantly expressed, especially in IL-10RB+ cells among peripheral blood mononuclear cells (PBMCs) of pancreatic duct adenocarcinoma patients, compared to a normal control group, were analyzed. The results of the analysis are shown in Tables 4 and 5 below. In Table 5 below, grades of each biomarker were selected as grades A, B, C and D based on the change in the expression level thereof in the patient group compared to that in the normal control group.

TABLE 4

| Gene name | Protein name | P value | Naïve_IL-10RB− | Naïve_IL-10RB+ |
|---|---|---|---|---|
| FLT3LG | Fms-Like Tyrosine Kinase 3 Ligand | 2.17768E−11 | 0.020851188 | 0.063721708 |
| CD27 | TNFRSF7 | 1.86034E−06 | 0.080887909 | 0.030795115 |
| IL-7R | Interleukin 7 receptor | 2.95039E−06 | 0.048373331 | 0.010340613 |
| IL-32 | Interleukin 32 | 0.000397908 | 0.333214524 | 0.218254857 |

TABLE 5

| GRADE | Gene | name | p_val | Naïve_IL10RB− | PDAC_IL10RB+ |
|---|---|---|---|---|---|
| A | CSF1R | Colony stimulating factor 1 receptor; CSF1R | 9.11781E−98 | 0.284661785 | 0.847480139 |
| A | CXCL16 | Chemokine (C-X-C motif) ligand 16 | 2.97717E−44 | 0.173089069 | 0.433164636 |
| A | TNFRSF1B | TNF receptor superfamily member 1B | 2.91423E−42 | 0.734350901 | 1.159456231 |
| C | CX3CR1 | CX3C chemokine receptor 1; CXCR1 | 1.21369E−41 | 0.335183671 | 0.656260057 |
| A | CSF3R | Colony stimulating factor 3 receptor | 1.28693E−36 | 0.935711945 | 0.527110739 |
| C | TNFRSF14 | TNF receptor superfamily member 14 | 4.47865E−32 | 0.265530815 | 0.492608351 |
| C | TNFSF13B | TNF receptor superfamily member 13B | 6.19882E−15 | 1.248885548 | 0.985380628 |
| C | TNF | Tumor necrosis factor-alpha | 1.06559E−13 | 0.01244331 | 0.066787124 |

TABLE 5-continued

| GRADE | Gene | name | p_val | Naïve_IL10RB⁻ | PDAC_IL10RB⁺ |
|---|---|---|---|---|---|
| A | PPBP | C-X-C Motif Chemokine 7 | 1.62062E−12 | 0.152079303 | 0.050534941 |
| B | TNFSF10 | TNF superfamily member 10, TRAIL, CD253, Apo-2L | 1.02773E11 | 0.485486986 | 0.624303941 |
| A | IL10RB | Interleukin 10 Receptor Subunit Beta | 1.86349E−11 | 0.321019084 | 0.422021664 |
| A | FLT3LG | Fms Related Tyrosine Kinase 3 Ligand | 2.17768E−11 | 0.020851188 | 0.063721708 |
| A | TNFRSF8 | TNF receptor superfamily member 8, CD30L Receptor, CD30, Ki-1 Antigen | 3.5984E−11 | 0.039764965 | 0.09114452 |
| B | IL10RA | Interleukin 10 receptor alpha subunit | 8.96479E11 | 0.369983726 | 0.480810254 |
| B | CKLF | Chemokine Like Factor | 2.10306E−10 | 1.026503487 | 0.81316181 |
| B | IL12RB1 | Interleukin 12 Receptor Subunit Beta 1 | 4.81611E−10 | 0.050354795 | 0.096078879 |
| A/B | CXCL10 | CXC Motif Chemokine 10 | 4.04881E−08 | 0.010635188 | 0.063392035 |
| B | LTBR | Lymphotoxin beta receptor, TNFRSF3 | 4.56476E−08 | 0.150942742 | 0.205881407 |
| A | PF4 | CXC Motif Chemokine 4, Platelet factor 4 | 4.98422E−08 | 0.090398507 | 0.027273622 |
| B | CD40 | CD40, TNFRSF5 | 5.50425E−08 | 0.036005134 | 0.071015021 |
| C | IFNGR1 | Interferon Gamma Receptor 1, CD119 | 5.59763E−08 | 0.378720037 | 0.459406945 |
| C | IFNAR1 | Interferon Alpah And Beta Receptor Subunit 1 | 5.61082E−08 | 0.18873117 | 0.235529872 |
| C | IL2RG | Interleukin 2 Receptor Subunit Gamma, CD132 | 1.71252E−07 | 0.178278334 | 0.222556365 |
| B | IL1B | Interleukin 1 beta | 2.08465E−07 | 0.073138315 | 0.141224125 |
| C | IL15 | Interleukin 15 | 2.11172E−07 | 0.157803933 | 0.197796608 |
| A | CD27 | TNFRSF7, CD27, S152, Tp55 | 1.86034E−06 | 0.080887909 | 0.030795115 |

TABLE 5-continued

| GRADE | Gene | name | p_val | Naïve_IL10RB⁻ | PDAC_IL10RB⁺ |
|---|---|---|---|---|---|
| C | EBI3 | Epstein-Barr virus induced gene 3, Interleukin 27 beta(IL27B) Interleukin 35 beta(IL35B) | 2.13937E−06 | 0.001002257 | 0.020729713 |
| B | RETN | Resistin, FIZZ3, C/EBP-Epsilon Regulated Myeloid Specific Secreted Cysteine-Rich Protein | 2.32009E−06 | 0.470588102 | 0.282306287 |
| A | IL7R | Interleukin 7 receptor | 2.95039E−06 | 0.048373331 | 0.010340613 |
| C | CCR2 | C-C chemokine receptor type 2 | 4.36492E−06 | 0.180484969 | 0.108218752 |
| C | IL16 | Interleukin 16 | 5.68272E−06 | 0.234139867 | 0.27388647 |
| A/B | IL21R | Interleukin 21 receptor, CD360 | 1.32497E−05 | 0.016111907 | 0.033939804 |
| B | IL2RB | Interleukin 2 receptor subunit beta | 2.34253E−05 | 0.01800926 | 0.04014119 |
| A/B | CCR5 | C-C chemokine receptor type 5 | 3.62575E−05 | 0.002752371 | 0.019863069 |
| C | IFNAR2 | Interferon Alpha And Beta Receptor Subunit 2 | 5.97599E05 | 0.19018063 | 0.21960771 |
| B | XCL2 | X-C Motif Chemokine Ligand 2 | 0.000103971 | 0.003095645 | 0.017843578 |
| A | IL32 | Interleukin 32 | 0.000397908 | 0.333214524 | 0.218254857 |
| C | TGFB1 | Transforming growth factor beta 1 | 0.000618962 | 0.674258755 | 0.734503831 |
| C | IFNGR2 | Interferon gamma receptor 2 | 0.000754282 | 0.777587331 | 0.852751697 |
| C | IL13RA1 | Interleukin 13 receptor, alpha 1 | 0.000779455 | 0.333202692 | 0.238606307 |
| B | CCL3 | C-C chemokine ligand 3 | 0.000788135 | 0.041033131 | 0.07103564 |
| C | CD4 | CD4 | 0.00124332 | 0.611316639 | 0.653220277 |
| D | TNFSF4 | Tumor necrosis factor ligand superfamily member 4 | 0.00143276 | 0.004519993 | 0 |
| C | EPOR | Erythropoietin receptor | 0.001455721 | 0.022639916 | 0.035051376 |
| B | TNFRSF17 | Tumor necrosis factor ligand superfamily member 17 | 0.001630524 | 0.018851853 | 0.006218546 |
| C | IL3RA | Interleukin 3 receptor subunit alpha | 0.001731577 | 0.013799956 | 0.021284064 |
| C | MIF | macrophage migration inhibitory factor | 0.002413924 | 0.711256529 | 0.775989712 |

TABLE 5-continued

| GRADE | Gene | name | p_val | Naïve_IL10RB⁻ | PDAC_IL10RB⁺ |
|---|---|---|---|---|---|
| B | CXCR4 | C-X-C Motif Chemokine receptor 4 | 0.002733879 | 0.124949625 | 0.072742326 |
| B | TNFRSF18 | Tumor necrosis factor ligand superfamily member 18 | 0.002919496 | 0.001271501 | 0.008807401 |
| C | CMTM6 | CKLF-like MARVEL transmembrane domain containing protein 6 | 0.003749227 | 0.757237117 | 0.820752754 |
| C | CMTM7 | CKLF-like MARVEL transmembrane domain containing protein 7 | 0.004946632 | 0.41201648 | 0.428916439 |
| C | TNFSF12 | Tumor necrosis factor ligand superfamily member 12 | 0.006929679 | 0.078884062 | 0.085758974 |
| A | IL23A | Interleukin 23 subunit alpha | 0.009847488 | 0.012866874 | 0.003297754 |
| B | TGFB3 | Transforming growth factor beta 3 | 0.011105785 | 0.005651646 | 0.000726786 |
| B | XCL1 | Chemokine (C motif) ligand | 0.012830511 | 0.002229976 | 0.009420969 |
| A/B | IL27 | Interleukin 27 | 0.015012659 | 0.005311122 | 0.014088945 |
| C | CXCL3 | Chemokine (C-X-C motif) ligand 3 | 0.018661077 | 0 | 0.003895959 |
| C | CCL5 | Chemokine (C-C motif) ligand 5 | 0.021636768 | 0.41077681 | 0.299725513 |
| C | CCL4L2 | C-C motif chemokine ligand 4 like 2 | 0.025857205 | 0.007086915 | 0.015547415 |
| B | IL7 | Interleukin 7 | 0.037149717 | 0 | 0.003785735 |
| D | HGF | Hepatocyte growth factor | 0.037163026 | 0.053581253 | 0.056236028 |
| B | KIT | receptor tyrosine kinases | 0.037831538 | 0.001401898 | 0.000200558 |
| B | CD40LG | CD40 ligand, CD154 | 0.03944883 | 0.008931828 | 0.002671554 |
| B | IL6ST | Interleukin 6 signal transducer | 0.042302409 | 0.143259092 | 0.091220512 |
| C | IL6R | Interleukin 6 receptor | 0.047743896 | 0.280818466 | 0.207943125 |
| C | CD70 | CD70 | 0.052484351 | 0.006993966 | 0.002399669 |
| C | MST1 | macrophage-stimulation protein | 0.05257586 | 0.006048124 | 0.002244745 |
| C | CXCL2 | Chemokine (C-X-C motif) ligand 2 | 0.063126585 | 0.002185765 | 0.004477288 |
| C | TNFSF14 | Tumor necrosis factor ligand superfamily member 14 | 0.064138217 | 0.023150125 | 0.0137085 |
| C | FLT3 | fms related tyrosine kinase 3 | 0.065231536 | 0.065851009 | 0.044541523 |
| B | IL1R2 | Interleukin 1 receptor, type 2 | 0.078861992 | 0.004953866 | 0.009368026 |
| C | TGFBR2 | Transforming growth factor beta receptor 2 | 0.106097301 | 0.242254247 | 0.222822872 |

TABLE 5-continued

| GRADE | Gene | name | p_val | Naïve_IL10RB⁻ | PDAC_IL10RB⁺ |
|---|---|---|---|---|---|
| C | IL6 | Interleukin 6 | 0.111194213 | 0.001125425 | 0 |
| C | LIF | Leukemia inhibitory factor | 0.111194213 | 0.001615341 | 0 |
| C | CXCR6 | C-X-C chemokine receptor type 6 | 0.111194213 | 0.001750627 | 0 |
| C | CXCL1 | Chemokine (C-X-C motif) ligand 1 | 0.114758202 | 0.004269771 | 0.000962623 |
| C | CCR7 | C-C chemokine receptor type 7 | 0.118661012 | 0.014225034 | 0.006409854 |
| C | CXCL11 | Chemokine (C-X-C motif) ligand 11 | 0.124041939 | 0 | 0.002087544 |
| B | GDF15 | growth differentiation factor 15 | 0.124041939 | 0 | 0.001910754 |
| C | IL1RN | Interleukin 1 receptor antagonist | 0.124343873 | 0.158976533 | 0.123695833 |
| D | IL11RA | Interleukin 11 receptor subunit alpha | 0.141905724 | 0.00902092 | 0.013163973 |
| C | TNFSF8 | Tumor necrosis factor ligand superfamily member 8 | 0.167848948 | 0.035313524 | 0.019555954 |
| D | IL15RA | Interleukin 15 receptor subunit alpha | 0.176000369 | 0.033004522 | 0.032324754 |
| D | CCL2 | Chemokine (C-C motif) ligand 2 | 0.183466045 | 0.030971785 | 0.020641778 |
| D | TNFRSF10A | Tumor necrosis factor receptor superfamily member 10a | 0.18549341 | 0.007553731 | 0.010408639 |
| D | CXCL8 | Chemokine (C-X-C motif) ligand 8 | 0.188208925 | 0.020257299 | 0.00750867 |
| D | CCL8 | Chemokine (C-C motif) ligand 8 | 0.199491894 | 0.001605797 | 0.004965616 |
| D | FAS | Fas | 0.200554416 | 0.063607406 | 0.056656713 |
| D | CCR4 | C-C chemokine receptor type 4 | 0.209355886 | 0 | 0.001716102 |
| D | CCL23 | Chemokine (C-C motif) ligand 23 | 0.209355886 | 0 | 0.001374009 |
| D | ACKR3 | Atypical chemokine receptor 3 | 0.209355886 | 0 | 0.001116842 |
| D | TNFSF18 | Tumor necrosis factor ligand superfamily member 18 | 0.209355886 | 0 | 0.001354822 |
| D | LTA | Lymphotoxin alpha | 0.22234073 | 0.005919625 | 0.0068245 |
| D | CCR10 | C-C chemokine receptor type 10 | 0.222908177 | 0.0067853 | 0.002565713 |
| D | CLCF1 | Cardiotrophin-like cytokine factor 1 | 0.246949272 | 0.003861854 | 0.006449803 |
| D | CCL4 | Chemokine (C-C motif) ligand 4 | 0.248374123 | 0.059487415 | 0.059633488 |

TABLE 5-continued

| GRADE | Gene | name | p_val | Naïve_IL10RB⁻ | PDAC_IL10RB⁺ |
|---|---|---|---|---|---|
| C | IL9R | Interleukin 9 receptor | 0.277075253 | 0 | 0.001232111 |
| C | IFNR1 | Interferon lambda receptor 1 | 0.277075253 | 0 | 0.000845322 |
| D | TGFBR1 | Transforming growth factor beta receptor 1 | 0.277167193 | 0.070147587 | 0.062445837 |
| D | TNFRSF10B | Tumor necrosis factor receptor superfamily member 10b | 0.280128382 | 0.090496295 | 0.079492009 |
| D | CSF2RB | Cytokine receptor common subunit beta | 0.302597637 | 0.176831966 | 0.150784921 |
| D | TGFA | Transforming growth factor alpha | 0.309036774 | 0.009591519 | 0.003346253 |
| D | CXCL9 | Chemokine (C-X-C motif) ligand 9 | 0.322678934 | 0.003248331 | 0.003209156 |
| D | TNFRSF1A | Tumor necrosis factor receptor superfamily member 1a | 0.328765843 | 0.467359709 | 0.433744752 |
| D | OSM | Oncostatin M | 0.330158441 | 0.002674441 | 0.005184151 |
| D | IL4R | Interleukin 4 receptor | 0.367274984 | 0.112099347 | 0.099094283 |
| D | PF4V1 | Platelet factor 4 variant 1 | 0.374976688 | 0 | 0.001324035 |
| D | PDGFB | Platelet Derived Growth Factor Subunit B | 0.374976688 | 0 | 0.000669628 |
| D | CCL20 | Chemokine (C-C motif) ligand 20 | 0.374976688 | 0 | 0.000584681 |
| D | IL12RB2 | Interleukin 12 receptor subunit beta 2 | 0.374976688 | 0 | 0.000863126 |
| D | CCL25 | Chemokine (C-C motif) ligand 25 | 0.374976688 | 0 | 0.00580123 |
| D | TGFBR3 | Transforming growth factor beta receptor 3 | 0.375008869 | 0.009011034 | 0.007969154 |
| D | IL17RA | Interleukin 17 eceptor subunit alpha | 0.390851067 | 0.431886939 | 0.359823626 |
| D | IL2RA | Interleukin 2 eceptor subunit alpha | 0.412248665 | 0.000786814 | 0.0014688 |
| D | TNFRSF10C | Tumor necrosis factor receptor superfamily member 10c | 0.413513995 | 0.01718871 | 0.015252352 |
| C | CXCR3 | C-X-C chemokine receptor type 3 | 0.438677072 | 0.010851236 | 0.006682484 |
| D | IL20RB | Interleukin 20 receptor subunit beta | 0.494545798 | 0.001055674 | 0.000388273 |
| D | CXCL5 | Chemokine (C-X-C motif) ligand 5 | 0.494545798 | 0.000778096 | 0.00024407 |
| D | IL5RA | Interleukin 5 receptor subunit alpha | 0.495101812 | 0.000792311 | 0.000431045 |

TABLE 5-continued

| GRADE | Gene | name | p_val | Naïve_IL10RB⁻ | PDAC_IL10RB⁺ |
|---|---|---|---|---|---|
| D | CXCR5 | C-X-C chemokine receptor type 5 | 0.528429179 | 0.000776399 | 0.001535715 |
| D | TNFRSF11A | Tumor necrosis factor receptor superfamily member 11a | 0.5290942 | 0.00105724 | 0.001545943 |
| C | IL24 | Interleukin 24 | 0.530699127 | 0 | 0.0046147 |
| C | SPP1 | secreted phosphoprotein 1 | 0.530699127 | 0 | 0.00035776 |
| D | CCL22 | Chemokine (C-C motif) ligand 22 | 0.530699127 | 0 | 0.000180201 |
| D | CCR9 | C-C chemokine receptor type 9 | 0.530699127 | 0 | 0.000145309 |
| D | CCL26 | Chemokine (C-C motif) ligand 26 | 0.530699127 | 0 | 0.000246975 |
| D | CX3CL1 | Chemokine (C-X3-C motif) ligand 1 | 0.530699127 | 0 | 0.000220785 |
| D | CXCL12 | Chemokine (C-X-C motif) ligand 12 | 0.530699127 | 0 | 0.000200006 |
| D | CMTM1 | CKLF-like MARVEL transmembrane domain containing protein 1 | 0.530699127 | 0 | 0.000192118 |
| D | TNFRSF10D | Tumor necrosis factor receptor superfamily member 10d | 0.552826577 | 0.022394655 | 0.020118013 |
| D | CCR3 | C-C chemokine receptor type 3 | 0.558547717 | 0.002502671 | 0.000954515 |
| D | CXCR1 | C-X-C chemokine receptor type 1 | 0.559296492 | 0.001929918 | 0.001071554 |
| D | CCL3L3 | C-C motif chemokine ligand 3 like 3 | 0.666217059 | 0.027143121 | 0.022980482 |
| D | CXCR2 | C-X-C chemokine receptor type 2 | 0.675463143 | 0.014259534 | 0.009718063 |
| D | IFNL1 | Interferon lambda 1 | 0.681029628 | 0.000508742 | 0.001420663 |
| D | IL18R1 | Interleukin 18 receptor, type 1 | 0.68659204 | 0.000971852 | 0.001873861 |
| D | TNFSF15 | Tumor necrosis factor ligand superfamily member 15 | 0.732158316 | 0.004169789 | 0.001803587 |
| D | CCR1 | C-C chemokine receptor type 1 | 0.739465525 | 0.277919651 | 0.230061173 |
| D | TNFRSF13B | Tumor necrosis factor receptor superfamily member 13b | 0.76902508 | 0.009186383 | 0.00658467 |
| D | TNFSF13 | Tumor necrosis factor ligand superfamily member 13 | 0.791645274 | 0.007991232 | 0.006706977 |
| D | IL18 | Interleukin 18 | 0.838507015 | 0.102661703 | 0.088072155 |
| D | FASLG | Fas ligand | 0.839694825 | 0.001778492 | 0.001604761 |
| D | IFNG | Interferon gamma | 0.88448231 | 0.000801789 | 0.001318267 |

TABLE 5-continued

| GRADE | Gene | name | p_val | Naïve_IL10RB⁻ | PDAC_IL10RB⁺ |
|---|---|---|---|---|---|
| D | PDGFRB | Platelet-derived growth factor receptor beta | 0.885956263 | 0.000817556 | 0.000819006 |
| D | TNFRSF25 | Tumor necrosis factor receptor superfamily member 25 | 0.920078162 | 0.016502453 | 0.010251106 |
| D | XCR1 | X-C Motif Chemokine Receptor 1 | 0.940271217 | 0.001834387 | 0.003460317 |
| D | IL1R1 | Interleukin 1 receptor, type 1 | 0.941466614 | 0.002638705 | 0.002971385 |
| D | TNFRSF9 | Tumor necrosis factor receptor superfamily member 9 | 0.984982929 | 0.001938184 | 0.001716434 |
| D | IL12A | Interleukin 12 receptor subunit alpha | 0.984982929 | 0.002164432 | 0.001804813 |
| D | CSF2RA | Colony stimulating factor 2 receptor subunit alpha | 0.989720078 | 0.268981715 | 0.215082988 |
| | TNFRSF4 | Tumor necrosis factor receptor superfamily member 4 | 0.124343873 | 0.158976533 | 0.123695833 |
| | CSF1 | Colony stimulating factor 1 | 0.139039754 | 0.013539027 | 0.00398904 |
| | IL17C | Interleukin 17C | 0.984982929 | 0.002164432 | 0.001804813 |
| | IL2 | Interleukin 2 | 0.989720078 | 0.268981715 | 0.215082988 |
| | IL26 | Interleukin 26 | NA | 0 | 0 |
| | IL4 | Interleukin 4 | NA | 0 | 0 |
| | PDGFA | Platelet-derived growth factor subunit A | NA | 0 | 0 |
| | TNFSF11 | Tumor necrosis factor ligand superfamily member 11 | NA | 0 | 0 |
| | TNFSF9 | Tumor necrosis factor ligand superfamily member 9 | NA | 0 | 0 |
| | CCR6 | C-C chemokine receptor type 6 | NA | 0 | 0 |
| | CCL19 | Chemokine (C-C motif) ligand 19 | NA | 0 | 0 |
| | MST1R | macrophage stimulating 1 receptor | NA | 0 | 0 |
| | TNFRSF11B | Tumor necrosis factor receptor superfamily member 11b | NA | 0 | 0 |
| | IL23R | Interleukin 23 receptor | NA | 0 | 0 |

TABLE 5-continued

| GRADE | Gene | name | p_val | Naïve_IL10RB⁻ | PDAC_IL10RB⁺ |
|---|---|---|---|---|---|
| | PDGFRA | Platelet-derived growth factor receptor A | NA | 0 | 0 |
| | CXCL13 | Chemokine (C-X-C motif) ligand 13 | NA | 0 | 0 |
| | EGF | Epidermal growth factor | NA | 0 | 0 |
| | IL13 | Interleukin 13 | NA | 0 | 0 |

[Experimental Example 2] Identification of Pancreatic Cancer-Specific Biomarkers (2)

1. Comparison of Expression Levels of Biomarkers in Normal Control Group and Pancreatic Cancer Patients Peripheral blood mononuclear cells (PBMC) were isolated from blood samples derived from a normal control group (n=31) and a pancreatic cancer patient group (n=38). RNA was isolated from the cells (Qiagen, USA) and then synthesized into cDNA using PrimeScript RT Master Mix (Perfect Real Time, Takara #RR036A), and PCR was performed using a StepOnePlus (AB Company) PCR system. The primer sequences used in the PCR are shown in Table 6 below. The results of comparing the mRNA expression levels of IL-7R, IL-32, FLT3LG, and IL-10RA in the normal control and the pancreatic cancer patient group samples using qPCR as described above are shown in FIGS. 2 to 5. A decrease in ΔCt indicates an increase in the mRNA expression level.

The results of performing statistical analysis using a ROC curve (Receiver Operating Characteristic curve) graph based on the qPCR results for each marker are shown in FIGS. 6 to 9, and the sensitivity and specificity values based on the AUC values and the cut-off values of ΔCt for each marker are shown in Tables 7 to 14 below.

TABLE 6

| Biomarker | Primer | Sequence |
|---|---|---|
| IL7R (Ref. NM_002185.5) | Forward Primer | GTAGTCATCACTCCAGAA AGC (SEQ ID NO: 5) |
| | Reverse Primer | ACCTGGAAGAGGAGAGAA TAG (SEQ ID NO: 6) |
| IL32 (Ref. NM_001012631.2) | Forward Primer | CAGAGCTCACTCCTCTAC TTGAA (SEQ ID NO: 7) |
| | Reverse Primer | GAACCATCTCATGACCTT GTCAC (SEQ ID NO: 8) |
| IL10RA (Ref. NM_001558.3) | Forward Primer | ACTTCAGCCTCCTAACCT CTG (SEQ ID NO: 9) |
| | Reverse Primer | AGGGAGATGCACTCCTCT TTAG (SEQ ID NO: 10) |
| FLT3LG (Ref. NM_001204502.1) | Forward Primer | TGGAGCCCAACAACCTAT CT (SEQ ID NO: 11) |
| | Reverse Primer | TAGTCAGACAGCTCACGG ATTT (SEQ ID NO: 12) |

TABLE 7

| IL-7R biomarker | |
|---|---|
| Area under the ROC curve | |
| Area (AUC) | 0.8184 |
| Std. Error | 0.05323 |
| 95% confidence interval | 0.7141 to 0.9228 |
| P value | <0.0001 |

TABLE 8

IL-7R biomarker

| Cut-off | Sensitivity % | 95% CI | Specificity % | 95% CI | Likelihood ratio |
|---|---|---|---|---|---|
| <2.152 | 73.68 | 56.90% to 86.60% | 80 | 61.43% to 92.29% | 3.68 |
| <2.186 | 73.68 | 56.90% to 86.60% | 76.67 | 57.72% to 90.07% | 3.16 |
| <2.231 | 76.32 | 59.76% to 88.56% | 76.67 | 57.72% to 90.07% | 3.27 |
| <2.260 | 76.32 | 59.76% to 88.56% | 73.33 | 54.11% to 87.72% | 2.86 |
| <2.273 | 78.95 | 62.68% to 90.45% | 73.33 | 54.11% to 87.72% | 2.96 |
| <2.283 | 81.58 | 65.67% to 92.26% | 73.33 | 54.11% to 87.72% | 3.06 |

TABLE 9

| IL-32 biomarker | |
|---|---|
| Area under the ROC curve | |
| Area (AUC) | 0.8095 |
| Std. Error | 0.05738 |
| 95% confidence interval | 0.6970 to 0.9220 |
| P value | <0.0001 |

TABLE 10

IL-32 biomarker

| Cut-off | Sensitivity % | 95% CI | Specificity % | 95% CI | Likelihood ratio |
|---|---|---|---|---|---|
| <1.152 | 71.43 | 53.70% to 85.36% | 86.67 | 69.28% to 96.24% | 5.36 |
| <1.205 | 71.43 | 53.70% to 85.36% | 83.33 | 65.28% to 94.36% | 4.29 |
| <1.270 | 74.29 | 56.74% to 87.51% | 83.33 | 65.28% to 94.36% | 4.46 |

TABLE 10-continued

| IL-32 biomarker | | | | | |
|---|---|---|---|---|---|
| Cut-off | Sensitivity % | 95% CI | Specificity % | 95% CI | Likelihood ratio |
| <1.290 | 74.29 | 56.74% to 87.51% | 80.00 | 61.43% to 92.29% | 3.71 |
| <1.294 | 77.14 | 59.86% to 89.58% | 80.00 | 61.43% to 92.29% | 3.86 |
| <1.415 | 80.00 | 63.06% to 91.56% | 80.00 | 61.43% to 92.29% | 4.00 |
| <1.538 | 80.00 | 63.06% to 91.56% | 76.67 | 57.72% to 90.07% | 3.43 |
| <1.588 | 80.00 | 63.06% to 91.56% | 73.33 | 54.11% to 87.72% | 3.00 |
| <1.643 | 82.86 | 66.35% to 93.44% | 73.33 | 54.11% to 87.72% | 3.11 |

TABLE 11

| FLT3LG biomarker | |
|---|---|
| Area under the ROC curve | |
| Area (AUC) | 0.7500 |
| Std. Error | 0.06245 |
| 95% confidence interval | 0.6276 to 0.8724 |
| P value | 0.0005628 |

TABLE 12

| FLT3LG biomarker | | | | | |
|---|---|---|---|---|---|
| Cut-off | Sensitivity % | 95% CI | Specificity % | 95% CI | Likelihood ratio |
| <4.390 | 73.68 | 56.90% to 86.60% | 78.57 | 59.05% to 91.70% | 3.44 |

TABLE 13

| IL-10RA biomarker | |
|---|---|
| Area under the ROC curve | |
| Area (AUC) | 0.755 |
| Std. Error | 0.05959 |

TABLE 13-continued

| IL-10RA biomarker | |
|---|---|
| Area under the ROC curve | |
| 95% confidence interval | 0.6387 to 0.8724 |
| P value | 0.0003 |

TABLE 14

| IL-10RA biomarker | | | | | |
|---|---|---|---|---|---|
| Cut-off | Sensitivity % | 95% CI | Specificity % | 95% CI | Likelihood ratio |
| <1.787 | 63.89 | 46.22% to 79.18% | 80.00 | 61.43% to 92.29% | 3.19 |
| <1.815 | 63.89 | 46.22% to 79.18% | 76.67 | 57.72% to 90.07% | 2.74 |
| <1.834 | 66.67 | 49.03% to 81.44% | 76.67 | 57.72% to 90.07% | 2.86 |
| <1.854 | 69.44 | 51.89% to 83.65% | 76.67 | 57.72% to 90.07% | 2.98 |
| <1.875 | 69.44 | 51.89% to 83.65% | 73.33 | 54.11% to 87.72% | 2.60 |
| <1.888 | 69.44 | 51.89% to 83.65% | 70.00 | 50.60% to 85.27% | 2.31 |
| <1.933 | 72.22 | 54.81% to 85.80% | 70.00 | 50.60% to 85.27% | 2.41 |

As shown in FIGS. 2 to 5, it was confirmed that the ΔCt values of IL-7R, IL-32, FLT3LG and IL-10RA in the peripheral blood mononuclear cells collected from the blood samples derived from the pancreatic cancer patients were lower than those in the normal control group, suggesting that the mRNA expression levels of IL-7R, IL-32, FLT3LG and IL-10RA in the peripheral blood mononuclear cells derived from the pancreatic cancer patients significantly increased compared to those in the normal control group.

As shown in FIGS. 6 to 9 and Tables 7 to 14 above, it can be seen that the IL-7R, IL-32, FLT3LG and IL-10RA biomarkers showed high sensitivity and specificity in pancreatic cancer diagnosis, suggesting that there is a statistical significance of pancreatic cancer diagnosis.

2. Statistical Analysis

Based on the results of Experimental Example 2-1, Shapiro-Wilk test, Kolmogorov-Smirnov test, independent two sample t-test, and logistic regression analysis for each marker or combinations of the markers were performed using SAS (version 9.3, SAS Inc., NC, USA) and PASS (version 12, NCSS, LLC, Kaysville, Utah, USA). The results of the analysis are shown in Tables 15 to 17 below.

TABLE 15

Shapiro-Wilk test and Kolmogorov-Smirnov test

| | Shapiro-Wilk test | | | Kolmogorov-Smirnov test | | |
|---|---|---|---|---|---|---|
| | Total (N = 68) | Control (N = 30) | Pancreatic cancer (N = 38) | Total (N = 68) | Control (N = 30) | Pancreatic cancer (N = 38) |
| IL-7R(ΔCt) | 0.4697 | 0.4726 | 0.4691 | 0.1359 | >0.1500 | 0.105 |
| IL-32(ΔCt) | 0.8153 | 0.1117 | 0.0122 | >0.1500 | >0.1500 | 0.0203 |
| FLT3LG(ΔCt) | 0.604 | 0.6507 | 0.0233 | >0.1500 | >0.1500 | 0.1487 |
| IL10RA(ΔCt) | 0.6982 | 0.2683 | 0.8054 | >0.1500 | >0.1500 | >0.1500 |

TABLE 16

| Independent two sample t-test (mean ± standard deviation) | | | | | |
|---|---|---|---|---|---|
| | Variable | Total (N = 68) | Control (N = 30) | Pancreatic cancer (N = 38) | p-value |
| Model 1 | PC1 | 1.984 ± 1.314 | 2.777 ± 1.049 | 1.358 ± 1.163 | <0.0001 |
| Model 2 | PC2 | 1.377 ± 1.152 | 1.944 ± 0.882 | 0.892 ± 1.144 | 0.0001 |
| Model 3 | PC3 | 4.388 ± 0.965 | 4.824 ± 0.778 | 4.066 ± 0.0973 | 0.0012 |
| Model 4 | PC4 | 1.887 ± 0.792 | 2.268 ± 0.656 | 1.570 ± 0.762 | 0.0002 |
| Model 5 | PC1 + PC2 | 0.538 ± 0.276 | 0.369 ± 0.230 | 0.684 ± 0.225 | <0.0001 |
| Model 6 | PC1 + PC3 | 0.576 ± 0.262 | 0.413 ± 0.224 | 0.695 ± 0.222 | <0.0001 |
| Model 7 | PC1 + PC4 | 0.545 ± 0.293 | 0.352 ± 0.240 | 0.706 ± 0.232 | <0.0001 |
| Model 8 | PC2 + PC3 | 0.556 ± 0.234 | 0.420 ± 0.194 | 0.664 ± 0.207 | <0.0001 |
| Model 9 | PC2 + PC4 | 0.538 ± 0.260 | 0.384 ± 0.212 | 0.671 ± 0.223 | <0.0001 |
| Model 10 | PC3 + PC4 | 0.562 ± 0.223 | 0.446 ± 0.189 | 0.653 ± 0.207 | 0.0001 |
| Model 11 | PC1 + PC2 + PC3 | 0.556 ± 0.264 | 0.394 ± 0.225 | 0.685 ± 0.220 | <0.0001 |
| Model 12 | PC1 + PC2 + PC4 | 0.538 ± 0.290 | 0.354 ± 0.239 | 0.697 ± 0.231 | <0.0001 |
| Model 13 | PC1 + PC3 + PC4 | 0.562 ± 0.285 | 0.377 ± 0.236 | 0.707 ± 0.233 | <0.0001 |
| Model 14 | PC2 + PC3 + PC4 | 0.556 ± 0.246 | 0.410 ± 0.200 | 0.672 ± 0.216 | <0.0001 |
| Model 15 | PC1 + PC2 + PC3 + PC4 | 0.556 ± 0.282 | 0.378 ± 0.235 | 0.698 ± 0.232 | <0.0001 |

(PC1: IL7R, PC2: IL32, PC3: FLT3LG, PC4: IL10RA)

TABLE 17

| Logistic regression analysis | | | | | | | |
|---|---|---|---|---|---|---|---|
| | Marker | OR (95% CI) | p-value | AUC (95% CI) | Optimal cut-off point | Sensitivity (95% CI) | Specificity (95% CI) |
| Model 1 | PC1 | 0.327 (0.186-0.574) | <0.0001 | 0.818 (0.713-0.923) | <2.283 | 0.816 (0.693-0.939) | 0.733 (0.575-0.892) |
| Model 2 | PC2 | 0.344 (0.184-0.645) | 0.0009 | 0.810 (0.696-0.923) | <1.415 | 0.800 (0.667-0.933) | 0.800 (0.657-0.943) |
| Model 3 | PC3 | 0.375 (0.194-0.724) | 0.0035 | 0.750 (0.627-0.873) | <4.39 | 0.737 (0.597-0.877) | 0.786 (0.634-0.938) |
| Model 4 | PC4 | 0.223 (0.089-0.561) | 0.0014 | 0.756 (0.638-0.873 | <1.8535 | 0.694 (0.544-0.845) | 0.767 (0.615-0.918) |
| Model 5 | PC1 | 0.383 (0.172-0.851) | 0.0185 | | | | |
| | PC2 | 0.798 (0.352-1.808) | 0.5886 | | | | |
| | PC1 + PC2 (p) | | | 0.822 (0.714-0.930) | ≥0.5043565 | 0.800 (0.667-0.933) | 0.833 (0.700-0.967) |
| Model 6 | PC1 | 0.340 (0.158-0.732) | 0.0059 | | | | |
| | PC3 | 1.001 (0.400-2.507 | 0.9981 | | | | |
| | PC1 + PC3 (p) | | | 0.807 (0.697-0.917) | ≥0.5868947 | 0.711 (0.566-0.855) | 0.821 (0.680-0.963) |
| Model 7 | PC1 | 0.403 (0.221-0.738) | 0.0032 | | | | |
| | PC4 | 0.416 (0.147-1.180) | 0.0991 | | | | |
| | PC1 + PC4 (p) | | | 0.846 (0.746-0.946) | ≥0.5438642 | 0.833 (0.712-0.955) | 0.867 (0.745-0.988) |

(PC1: IL7R, PC2: IL32, PC3: FLT3LG, PC4: IL10RA)

From the results in Tables 15 to 17 above, as a result of the normality test, it was confirmed that the IL-7R, IL-32, FLT3LG and IL-10RA biomarkers satisfied normality in pancreatic cancer diagnosis, and that the ability to diagnosis and predict pancreatic cancer was better when a combination of IL-7R and IL-10RA was measured than the markers were measured alone.

In addition, equations for predicting the likelihood of developing pancreatic cancer depending on the expression level of the combination of IL-7R and IL-10RA were derived.

$$LP = 3.7068 - 0.9077 \times (IL-7R) - 0.8776 \times (IL-10RA) \quad \text{[Equation 3]}$$

$$\text{Probability of developing pancreatic cancer} = 1/(1+\exp(-LP)) \quad \text{[Equation 4]}$$

In Equation 3 above, IL-7R and IL-10RA are ΔCt values which are IL-7R mRNA and IL-10RA mRNA expression levels, respectively, relative to the housekeeping gene (GADPH). It is possible to predict the likelihood of developing pancreatic cancer by substituting the LP value, obtained from Equation 3, into Equation 4 above.

In addition, using the results in Tables 15 to 17 above, the specificity and sensitivity of pancreatic cancer diagnosis depending on the combination of the cut-off values of IL-7R and IL-10RA were analyzed, and the results of the analysis are shown in Table 18 below. At this time, when two variables for the mRNA expression levels of IL-7R and IL-10RA, obtained in the patients, were greater than the cut-off value, a score of 0 points was given, and when only one of the two variables was smaller than the cut-off value and the other was greater than the cut-off value, a score of 1 point was given, and when the two variables were all smaller than the cut-off value, a score of 2 points was given. Then, the scores were cut off and the specificity and sensitivity for each cut off score were calculated.

TABLE 18

| | Component 1 | 0 | 1 | 2 |
|---|---|---|---|---|
| | | PC1 ≥ 2.283, PC4 ≥ 1.8535 | PC1 < 2.283, PC4 ≥ 1.8535 or PC1 ≥ 2.283, PC4 < 1.8535 | PC1 < 2.283, PC4 < 1.8535 |
| OR(95% CI) | | ref (1) | 4.111(1.013-16.691) | 27.602(5.827-130.743) |
| p-value | | | 0.048 | <.0001 |
| AUC(95% CI) | 0.828(0.731-0.924) | | | |
| Cut off point | | | ≥1 | ≥2 |
| Sensitivity (95% CI) | | | 0.889(0.786-0.992) | 0.639(0.482-0.796) |
| Specificity (95% CI) | | | 0.600(0.425-0.775) | 0.900(0.793-1.000) |

As shown in Table 18 above, it could be confirmed that, when the variable of IL-7R was less than 2.283 and the variable of IL-10RA was 1.8535 or more, or when the variable of IL-7R variable was 2.283 or more and the variable of IL-10RA was less than 1.8535, when the variable of IL-7R was less than 2.283 and the variable of IL-10RA was less than 1.8535, both the specificity and sensitivity of pancreatic cancer diagnosis were excellent.

[Experimental Example 3] Identification of Pancreatic Cancer-Specific Biomarkers (3)

1. Comparison of Expression Levels of Biomarkers in Normal Control Group and Pancreatic Cancer Patients Peripheral blood mononuclear cells (PBMC) were isolated from blood samples derived from a normal control group (n=31) and a pancreatic cancer patient group (n=38). RNA was isolated from the cells (Qiagen, USA) and then synthesized into cDNA using PrimeScript RT Master Mix (Perfect Real Time, Takara #RR036A), and PCR was performed using a StepOnePlus (AB Company) PCR system. The primer sequences used in the PCR are shown in Table 19 below. The results of comparing the mRNA expression levels of IL-7R, FLT3LG and CD27 in the normal control group sample and the pancreatic cancer patient group samples using qPCR as described above are shown in FIGS. 10 to 12. A decrease in ΔCt indicates an increase in the mRNA expression level.

The results of performing statistical analysis using a ROC curve (Receiver Operating Characteristic curve) graph based on the qPCR results for each marker are shown in FIGS. 13 to 15, and the sensitivity and specificity values based on the AUC values and the cut-off values of ΔCt for each marker are shown in Tables 20 to 22 below.

TABLE 19

| Biomarker | Primer | Sequence |
|---|---|---|
| IL7R (Ref. NM_002185.5) | Forward Primer | GTAGTCATCACTCCAGAA AGC (SEQ ID NO: 5) |
| | Reverse Primer | ACCTGGAAGAGGAGAGAA TAG (SEQ ID NO: 6) |
| FLT3LG (Ref. NM_001204502.1) | Forward Primer | TGGAGCCCAACAACCTAT CT (SEQ ID NO: 11) |
| | Reverse Primer | TAGTCAGACAGCTCACGG ATTT (SEQ ID NO: 12) |
| CD27 (Ref. NM_001242.4) | Forward Primer | GAAGGACTGTGACCAGCA TAGA (SEQ ID NO: 13) |
| | Reverse Primer | CGAACGAGAAGACCAGAGT TACA (SEQ ID NO: 14) |

TABLE 20

| IL-7R biomarker | |
|---|---|
| Area under the ROC curve | |
| Area (AUC) | 0.8280 |
| Std. Error | 0.04963 |
| 95% confidence interval | 0.7307 to 0.9253 |
| P value | <0.0001 |

TABLE 21

| FLT3LG biomarker | |
|---|---|
| Area under the ROC curve | |
| Area (AUC) | 0.7881 |
| Std. Error | 0.05708 |
| 95% confidence interval | 0.6762 to 0.9001 |
| P value | <0.0001 |

TABLE 22

| CD27 biomarker | |
|---|---|
| Area under the ROC curve | |
| Area (AUC) | 0.7437 |
| Std. Error | 0.07107 |
| 95% confidence interval | 0.6043 to 0.8830 |
| P value | 0.004223 |

As shown in FIGS. 10 to 12, it was confirmed that the ΔCt values of IL-7R, FLT3LG and CD27 in the peripheral blood mononuclear cells collected from the blood samples derived from the pancreatic cancer patients were lower than those in the normal control group, suggesting that the mRNA expression levels of IL-7R, FLT3LG and CD27 in the peripheral blood mononuclear cells derived from the pancreatic cancer patients significantly increased compared to those in the normal control group.

As shown in FIGS. 13 to 15 and Tables 20 to 22 above, it can be seen that the IL-7R, FLT3LG and CD27 biomarkers showed high sensitivity and specificity in pancreatic cancer diagnosis, suggesting that there is a statistical significance of pancreatic cancer diagnosis.

2. Statistical Analysis

Based on the results of Experimental Example 3-1, Mann-Whitney U test and logistic regression analysis for each marker or combinations of the markers were performed using SAS (version 9.3, SAS Inc., NC, USA) and PASS (version 12, NCSS, LLC, Kaysville, Utah, USA). The results of the analysis are shown in Tables 23 and 24 below. However, regarding the cut-off value, the point at which the Youden index, i.e., "sensitivity+specificity−1", was the maximum was determined as an optimal cut-off point, and a P value<0.05 was considered significant.

TABLE 23

| Mann-Whitney U test | | | |
|---|---|---|---|
| | Control (N = 30) | Pancreatic cancer (N = 42) | p-value |
| Age | 61 (52-70), (42-86) | 66.5(59-79), (38-84) | 0.0601 |
| Sex | | | 0.3390 |
| Male | 17(56.67) | 19(45.24) | |
| Female | 13(43.33) | 23(54.76) | |
| IL-7R | 2.778(2.254-3.537), (0.527-4.574) | 1.094(0.533-2.139), (−0.734-4.568) | <0.0001 |
| IL-32 | 2.027(1.541-2.402), (−0.149-3.244) | 0.761(0.302-1.296), (−0.976-4.982) | <0.0001 |
| FLT3LG | 4.86(4.463-5.314), (3.272-6.3) | 3.821(3.391-4.22), (2.354-7.491) | <0.0001 |
| IL-10RA | 2.211(1.87-2.509), (0.97-4.186) | 1.708(1.364-2.108), (0.128-3.228) | 0.0014 |
| CD27 | 4.972(4.045-5.881), (3.327-6.333) | 3.902(2.807-4.971), (1.749-6.07) | 0.0043 |

TABLE 24

| Logistic regression analysis | | | | | | | |
|---|---|---|---|---|---|---|---|
| | Biomarker | OR (95% CI) | p-value | AUC (95% CI) | Optimal cut-off point | Sensitivity (95% CI) | Specificity (95% CI) |
| Mode 11 | IL-7R | 0.341 (0.203-0.572) | <0.0001 | 0.823 (0.723-0.923) | 0.7206507<, >0.7206507 | 0.714 (0.578-0.851) | 0.867 (0.745-0.988) |
| Mode 12 | IL-32 | 0.372 (0.209-0.662) | 0.0008 | 0.798 (0.683-0.913) | 0.5523593<, >0.5523593 | 0.821 (0.700-0.941) | 0.800 (0.657-0.943) |
| Mode 13 | FLT3LG | 0.334 (0.174-0.642) | 0.001 | 0.787 (0.673-0.900) | 0.5926827<, >0.5926827 | 0.810 (0.691-0.928) | 0.786 (0.634-0.938) |
| Mode 14 | IL-10RA | 0.260 (0.105-0.649) | 0.0039 | 0.726 (0.605-0.847) | 0.5303559<, >0.5303559 | 0.744 (0.607-0.881)) | 0.667 (0.498-0.835) |
| Mode 15 | CD27 | 0.428 (0.238-0.768) | 0.0044 | 0.744 (0.603-0.884) | 0.7527883<, >0.7527883 | 0.417 (0.219-0.614) | 1.000 (1.000-1.000) |
| Mode 16 | IL-7R | 0.356 (0.100-1.261) | 0.1093 | | | | |
| | FLT3LG | 0.714 (0.227-2.248) | 0.5651 | | | | |
| | CD27 | 0.949 (0.395-2.280) | 0.9063 | | | | |
| | IL-7R + FLT3LG + CD27(p) | | | 0.830 (0.710-0.949) | 0.5400606<, ≥0.5400606 | 0.750 (0.577-0.923) | 0.826 (0.671-0.981) |

As shown in Tables 23 and 24 above, it can be seen that the IL-7R, IL-32, FLT3LG, IL-10RA and CD27 biomarkers showed high sensitivity and specificity in pancreatic cancer diagnosis, and thus there was a statistical significance of pancreatic cancer diagnosis. Additionally, through this Experimental Example, it was confirmed that the ability to diagnosis and predict pancreatic cancer was better when a combination of IL-7R, FLT3LG and CD27 was measured than the markers were measured alone.

In addition, using the results in Tables 23 and 24 above, equations for predicting the likelihood of developing pancreatic cancer depending on the expression levels of IL-7R, FLT3LG and CD27 were derived.

$$LP = 3.8688 - 1.0342 \times (IL-7R) - 0.3365 \times (FLT3LG) - 0.0526 \times (CD27) \quad \text{[Equation 5]}$$

$$\text{Probability of developing pancreatic cancer} = 1/(1+\exp(-LP)) \quad \text{[Equation 6]}$$

In Equation 5 above, IL-7R, FLT3LG and CD27 are ΔCt values which are IL-7R mRNA, FLT3LG mRNA and CD27 mRNA expression levels, respectively, relative to the housekeeping gene (GADPH). It is possible to predict the likelihood of developing pancreatic cancer by substituting the LP value, obtained from Equation 5, into Equation 6 above.

In addition, using the results in Tables 23 to 24 above, the specificity and sensitivity of pancreatic cancer diagnosis depending on the combination of the cut-off values of IL-7R, FLT3LG and CD27 were analyzed, and the results of the analysis are shown in Table 25 below. At this time, when the expression levels of two biomarkers among the IL-7R, FLT3LG and CD27, obtained in the patients, were greater than the cut-off value, a score of 0 points was given, and when only one of the three biomarkers was smaller than the cut-off value and the other two were greater than the cut-off value, a score of 1 point was given, and when two of the three biomarkers were smaller than the cut-off value, a score of 2 points was given, and the three biomarkers were all smaller than the cut-off value, a score of 3 points was given. Then, the scores were cut off and the specificity and sensitivity for each cut off score were calculated.

TABLE 25

| | Component 1 | 0 | 1 | 2 | 3 |
|---|---|---|---|---|---|
| | | 7R ≥ 0.7206507, T3 ≥ 0.5926827, 27 ≥ 0.7527883 | 7R < 0.7206507, T3 ≥ 0.5926827, 27 ≥ 0.7527883 or 7R ≥ 0.7206507, T3 < 0.5926827, 27 ≥ 0.7527883 or 7R ≥ 0.7206507, T3 ≥ 0.5926827, 27 < 0.7527883 | 7R < 0.7206507, T3 < 0.5926827, 27 ≥ 0.7527883 or 7R < 0.7206507, T3 ≥ 0.5926827, 27 < 0.7527883 or 7R ≥ 0.7206507, T3 < 0.5926827, 27 < 0.7527883 | 7R < 0.7206507, T3 < 0.5926827, 27 < 0.7527883 |
| OR(95% CI) | | ref(1) | 5.571(1.043-29.757) | 12.256(1.748-85.953) | 89.545(3.559-2246.524) |
| P-value | | | 0.0445 | 0.0117 | 0.0063 |
| AUC(95% CI) | 0.859(0.757-0.961) | | | | |
| Cut off point | | | ≥1 | ≥2 | ≥3 |
| Sensitivity (95% CI) | | | 0.875(0.743-1.000) | 0.625(0.431-0.819) | 0.375(0.181-0.569) |
| Specificity (95% CI) | | | 0.696(0.508-0.384) | 0.913(0.798-1.000) | 1.000(1.000-1.000) |

As shown in Table 25 above, it could be confirmed that, when the expression level of IL-7R was less than 0.7206507, the expression level of FLT3LG was 0.5926827 or more, and the expression level of CD27 was 0.7527883 or more, or when the expression level of IL-7R was 0.7206507 or more, the expression level of FLT3LG was less than 0.5926827, and the expression level of CD27 was 0.7527883 or more, or when the expression level of IL-7R was 0.7206507 or more, the expression level of FLT3LG was 0.5926827 or more, and the expression level of CD27 was less than 0.7527883, both the specificity and sensitivity of pancreatic cancer diagnosis were excellent.

[Experimental Example 4] Evaluation of Clinical Efficacy of Pancreatic Cancer-Specific Biomarkers In order to evaluate the clinical efficacy of the pancreatic cancer-specific biomarkers, the expression levels of the biomarkers were measured for a group of patients diagnosed with pancreatic cancer. Specifically, for patient A, who was diagnosed with T1 stage pancreatic cancer with a size of 0.6 cm×0.64 cm, and patient B, who was diagnosed with pancreatitis and was diagnosed with pancreatic cancer after 3 months of follow-up and had received surgery for pancreatic cancer, peripheral blood mononuclear cells were isolated. Thereafter, RNA was isolated from the cells (Qiagen, USA) and then synthesized into cDNA using PrimeScript RT Master Mix (Perfect Real Time, Takara #RR036A), and PCR was performed using a StepOnePlus (AB Company) PCR system. Then, the expression levels of the pancreatic cancer-specific biomarkers were measured in the same manner as in the above-described Experimental Example.

The experimental results for patient A are shown in Tables 26 and 27 below. Values in parentheses in Tables 26 and 27 below indicate ΔCt values for expression levels in a normal control.

TABLE 26

| PBMC_qPCR (ΔCt) | | hIL-7RA (<2.283) | hFLT3LG (<4.39) | hIL-22RA (<6.62 | CA19-9 (>24.0) |
|---|---|---|---|---|---|
| Patient A | 2017 Dec. 11 | 1.270 | 2.767 | 6.223 | 9.8 |

TABLE 27

| PBMC_FACS (% cells) | | IL-22RA (>5.5) | IL-10RB (>5.5) |
|---|---|---|---|
| Patient A | 2017 Dec. 11 | 5.65 | 8.17 |

As shown in Table 26 above, the expression of IL-7RA and FLT3LG mRNA increased in peripheral blood mononuclear cells derived from patient A, who was diagnosed with T1 stage pancreatic cancer, compared to the normal control, whereas the expression of the other markers, specifically CA9-9 and IL-22RA mRNA was within the normal range. In addition, as shown in Table 27 above, it could be confirmed that the expression of IL-22RA and IL-10RB proteins was also within the normal range.

The experimental results for patient B are shown in Tables 28 and 29 below. Values in parentheses in Tables 28 and 29 below indicate ΔCt values for expression levels in a normal control.

TABLE 28

| PBMC_qPCR (ΔCT) | | hIL-7RA (<2.283) | hFLT3LG (<4.39) | hCD27 (<3.21) |
|---|---|---|---|---|
| Time of diagnosis of pancreatitis | 2017 May 22 | 0.011 | 3.393 | 5.218 |
| Time of diagnosis of pancreatic cancer | 2017 Aug. 21 | −0.689 | 3.939 | 3.040 |
| Month 6 after pancreatic cancer surgery | 2018 Feb. 14 | 4.423 | 6.175 | 6.942 |

TABLE 29

| PBMC_qPCR (ΔCT) | | hIL-22RA (<6.62) | hIL-10RB (<4.53) |
|---|---|---|---|
| Time of diagnosis of pancreatic cancer | 2017 Aug. 21 | 8.113 | 6.023 |
| Month 6 after pancreatic cancer surgery | 2018 Feb. 14 | 8.54 | 3.317 |

As shown in Table 28 above, it was confirmed that, at the time of diagnosis of pancreatic cancer, the expression levels of IL-7RA, FLT3LG, and CD27 mRNA all increased in the peripheral blood mononuclear cells derived from patient B compared to the normal control group, and such increases in the expression levels were all restored to the normal ranges after pancreatic cancer surgery. In addition, as shown in Table 29, it could be confirmed that the expression levels of IL-22RA and IL-10RB mRNA at the time of pancreatic cancer diagnosis were within the normal ranges.

Taken together, these experimental results indicate that the pancreatic cancer-specific biomarkers according to one embodiment may be used as specific biomarkers in pancreatic cancer diagnosis, which have a function distinct from other biomarkers.

Experimental Example 5

Evaluation of Efficacy of Pancreatic Cancer-Specific Biomarkers Using Pancreatic Cancer Animal Model Evaluation of the efficacy of the pancreatic cancer-specific biomarkers using a pancreatic cancer animal model was performed as shown in FIG. 16. Specifically, $2\times10^6$ cells/20 μL of Pan02 PDAC cells (pancreatic ductal adenocarcinoma cell line, Pan02) were transplanted directly into the pancreas of each 8-week-old wild-type (WT) mouse (C57BL/6, OrientBio), thereby constructing an orthotopic pancreatic cancer mouse animal model. On days 2, 4, 5, 7, and 11 from the day the Pan02 PDAC cells were transplanted, the animal model was sacrificed, and the weight of each of tumor tissue and spleen was measured. In addition, after isolation of peripheral blood mononuclear cells from the blood of the animal model, FACS analysis was performed using an IL-7R, IL-22R1 or IL-10RB specific antibody (mIL7R, APC (BD, Cat. 564175), mAR, Percp (R&D, Cat. FAB42941C), or mBR, APC (R&D, Cat. FAB53681A)), and time-dependent changes in the expression of the biomarkers were examined by comparing the expression level of IL-7R, IL-22R1 or IL-10RB on the surfaces of the peripheral blood mononuclear cells. Meanwhile, in this Experimental Example, a group in which PBS was administered to the pancreas of 8-week-old wild-type (WT) mice (C57BL/6, OrientBio) was set as a control group.

As shown in FIG. 17, it was confirmed that the weights of tumor tissue and spleen in the pancreatic cancer animal model prepared in this Experimental Example increased over time, suggesting that the pancreatic cancer animal model was stably constructed.

In addition, as shown in FIG. 18, the expression levels of IL-7R and IL-22R in the peripheral blood mononuclear cells of the pancreatic cancer animal model significantly increased compared to that in the control group, whereas a significant change in the expression level of IL-10RB was not observed. In particular, the expression pattern of IL-7R significantly increased from the initial stage (day 4) of pancreatic cancer, and as the pancreatic cancer progressed, the expression level of IL-7R also tended to increase.

Taken together, these experimental results indicate that the pancreatic cancer-specific biomarkers according to one embodiment may be used not only for early diagnosis of pancreatic cancer, but also for evaluating the progression or prognosis of pancreatic cancer.

[Experimental Example 6] Analysis of Correlation Between Expression of IL-10RB in Peripheral Blood Mononuclear Cells (PBMCs) and Proliferation of Pancreatic Cancer Cells 1. Materials and Method 1-1. Analysis of Proliferation of Pancreatic Cancer Cells by CCK-8 Assay (Cell Proliferation Assay)

100 μl ($5\times10^3$ cells/well) of a PanO2 cell (pancreatic cancer cell) culture was inoculated into each well of 96-well plates (n=5), and pre-incubated in a humidified incubator at 37° C. under 5% $CO_2$.

The pancreatic cancer cell culture of each well was inoculated with 200 μl of IL-10RB$^+$ PBMC conditioned medium (CM) or IL-10RB$^-$ PBMC conditioned medium (CM). In addition, some experimental groups were inoculated with 2 μg/ml (R & D) or 1 μg/ml (Novus) anti-IL-10RB neutralizing antibody (neutralizing Ab). Then, each well was incubated for 24 hours, 48 hours, or 72 hours.

After incubation, each well of the 96-well plate was inoculated with 10 μl of CCK-8 solution, followed by incubation for 3 hours. Then, for the 96-well plate, the absorbance at 450 nm was measured using a microplate reader. The proliferation level of the pancreatic cancer cells was analyzed by calculating the fold increase in the absorbance value of the experimental group inoculated with the IL-10RB$^+$ PBMC conditioned medium (CM), relative to the absorbance value of the experimental group inoculated with the IL-10RB$^-$ PBMC conditioned medium (CM).

1-2. Analysis of Proliferation of Pancreatic Cancer Cells by FACS (Fluorescence-Activated Cell Sorting, Cell Counting) (Cell Proliferation Assay)

PanO2 cells ($3\times10^6$) were labeled with CellTracker™ Green CMFDA (5-chloromethylfluorescein diacetate), and then each well of 96-well plates (n=3) was inoculated with into the PanO2 cell culture ($1\times10^5$ cells/well).

The labeled pancreatic cancer culture of each well was inoculated with IL-10RB$^+$ PBMC conditioned medium (CM) or IL-10RB$^-$ PBMC conditioned medium (CM) at a concentration of $1\times10^5$ cells/well. In addition, some experimental groups were inoculated with 2 μg/ml (R & D) or 1 μg/ml (Novus) anti-IL-10RB neutralizing antibody (neutralizing Ab). Then, each well was incubated for 48 hours or 72 hours. Thereafter, the labeled pancreatic cancer cells were counted using a hemocytometer.

1-3. Statistical Analysis

All quantitative experiments were performed at least in triplicate (n=3 or n=5), and data values were expressed as mean±SD. The data values shown in FIGS. 19 to 23 were analyzed by two-tailed unpaired t test using GraphPad Prism 8.0.2. The data values shown in FIGS. 24 to 33 were analyzed by one-way Anova test using GraphPad Prism 8.0.2.

2. Confirmation of the Increase in Pancreatic Cancer Cell Proliferation Caused by Increased Expression of IL-10RB in PBMCs (Confirmation of the Function of IL-10RB as Biomarker Related to Pancreatic Cancer Cell Proliferation)

In this Experimental Example, in order to examine whether the proliferation of pancreatic cancer cells increases as the expression of IL-10RB in PBMCs increases, the proliferation level of pancreatic cancer cells was analyzed by CCK-8 assay and FACS analysis.

As a result, as shown in FIGS. 19 to 21, it was confirmed by CCK-8 assay that, when the pancreatic cancer cell culture was inoculated with IL-10RB$^+$ PBMC conditioned medium (CM), the proliferation of the pancreatic cancer cells significantly increased compared to when the pancreatic cancer cell culture was inoculated with IL-10RB$^-$ PBMC conditioned medium (CM).

Likewise, as shown in FIGS. 22 and 23, it was confirmed by FACS analysis that, when the pancreatic cancer cell culture was inoculated with IL-10RB$^+$ PBMC conditioned medium (CM), the proliferation of the pancreatic cancer cells significantly increased compared to when the pancreatic cancer cell culture was inoculated with IL-10RB$^-$ PBMC conditioned medium (CM).

Therefore, through this Experimental Example, it was confirmed that the proliferation of pancreatic cancer cells may be detected by measuring the expression level of IL-10RB in PBMCs, suggesting that IL-10RB may function as a biomarker related to the proliferation of pancreatic cancer cells.

3. Confirmation of Inhibition of Pancreatic Cancer Cell Proliferation by Inhibition of IL-10RB in PBMCs (Evaluation of Pancreatic Cancer Cell Proliferation Inhibitory Function of IL-10RB Inhibitor)

In this Experimental Example, in order to examine whether the proliferation of pancreatic cancer cells is inhibited by the inhibition of IL-10RB in PBMCs, the proliferation level of pancreatic cancer cells was analyzed through CCK-8 assay and FACS analysis.

As a result, as shown in FIGS. 24-33, it was confirmed that, when the pancreatic cancer cell culture was inoculated with IL-10RB$^+$ PBMC conditioned medium (CM), as the culture time increased, the proliferation of the pancreatic cancer cells significantly increased compared to when the pancreatic cancer cell culture was inoculated with IL-10RB$^-$ PBMC conditioned medium (CM). However, when the pancreatic cancer cell culture was additionally inoculated with an anti-IL-10RB neutralizing antibody (neutralizing Ab) which is an IL-10RB inhibitor, the increase in proliferation of the pancreatic cancer cells was inhibited even when the culture was inoculated with IL-10RB$^+$ PBMC conditioned medium (CM).

Through this Experimental Example, it was confirmed that the proliferation of pancreatic cancer cells can be inhibited by inhibiting IL-10RB in PBMCs. Specifically, inhibition of IL-10RB in PBMCs may lead to inhibition of the activity of IL-10RB protein or inhibition of the expression of a gene encoding IL-10RB. Therefore, the IL-10RB inhibitor is not limited to the anti-IL-10RB neutralizing antibody (neutralizing Ab) used in this Experimental Example, but may be any agent capable of inhibiting the activity of the IL-10RB protein or inhibiting the expression of the gene encoding IL-10RB, and this IL-10RB inhibitor may be used as an anticancer therapeutic agent that inhibits the proliferation of pancreatic cancer cells.

[Experimental Example 7] Analysis of Correlation of IL-10RB, IL-22, and Pancreatic Cancer Cell Proliferation 1. Confirmation of Inhibition of IL-10RB Expression in PBMCs of IL-22 Knockout (KO) Mice In this Experimental Example, in order to examine whether IL-10RB expression is inhibited in PBMCs of IL-22 KO mice, PBMCs were extracted from IL-22 KO mice and B6 mice (WT), and IL-10RB expression levels therein were measured. In addition, after the PanO2 cell line (pancreatic cancer cell line) was injected into the pancreas of IL-22 KO mice and B6 mice (WT), PBMCs around pancreatic cancer cells were extracted, and IL-10RB expression levels therein were measured. For reference, IL-22 is a cytokine encoded by the IL-22 gene. Although IL-22 stimulation results in activation of STAT1, STAT3 or STAT5, the physiological function of IL-22 is still unclear.

As a result, as shown in FIG. 34, it was confirmed that the cell number of IL-10RB$^+$ PBMCs in the IL-22 KO mice significantly decreased compared to that in the B6 mice (WT). In particular, as shown in FIG. 35, it was confirmed that, in the B6 mice (WT), the cell number of IL-10RB$^+$ PBMCs around pancreatic cancer cells increased significantly and the IL-10RB$^+$ PBMCs invaded the pancreatic cancer cells, whereas in the IL-22 KO mice, the cell number of IL-10RB$^+$ PBMCs around pancreatic cancer cells significantly decreased compared that in the B6 mice (WT).

Also, as shown in FIGS. 36 and 37, it was confirmed that, among the cells stained with CD11b among the PBMCs extracted from the IL-22 KO mice and the B6 mice (WT), the cell number of IL-10RB$^+$ PBMCs significantly decreased in the IL-22 KO mice compared to the B6 mice (WT).

Through this Experimental Example, it was confirmed that IL-10RB in PBMCs may be inhibited by completely removing the IL-22 gene or inhibiting the expression of the IL-22 gene. Therefore, the IL-22 gene inhibitor can inhibit the proliferation of pancreatic cancer cells, and thus can be used as an anticancer therapeutic agent, like an IL-10RB inhibitor.

2. Confirmation of Decrease in Pancreatic Cell Size and Restoration of Normal Immune System in IL-22 Knockout (KO) Mice In this Experimental Example, in order to confirm the specific pancreatic cancer treatment effect in IL-22 KO mice, the PanO2 cell line (pancreatic cancer cell line) was injected into the pancreas of IL-22 KO mice and B6 mice (WT), and analysis was made as to changes in the pancreatic cancer cells size and the recovery of lymph nodes (LN) around pancreatic cancer cells.

As a result, as shown in FIGS. 38 and 39, it was confirmed that the size of pancreatic cancer cells significantly decreased in the IL-22 KO mice compared to the B6 mice (WT).

In addition, as shown in FIGS. 40 and 41, it was confirmed that lymph glands around the pancreatic cancer cells in the IL-22 KO mice were activated and restored to their original shape. On the other hand, it was confirmed that, in the B6 mice (WT), the lymph glands were atrophied, and pancreatic cancer cells invaded the lymph glands.

Through this Experimental Example, it was confirmed that, when the IL-22 gene is completely removed or the expression of the IL-22 gene is inhibited, the size of pancreatic cancer cells may be decreased and the recovery of lymph nodes around pancreatic cancer cells may be induced. The following demonstrates whether inhibition of the IL-22 gene directly induces this effect or whether inhibition of the IL-22 gene indirectly induces this effect by inhibiting IL-10RB in PBMCs.

3. Analysis of Correlation Between IL-22 and IL-10RB by Examination of Whether Inhibition of IL-22 Directly Affects Pancreatic Cancer Cell Proliferation In this Experimental Example, in order to examine whether the inhibition of IL-22 directly affects the proliferation of pancreatic cancer cells, analysis was made as to the proliferation of pancreatic cancer cells when the activity of already expressed IL-22 protein was inhibited, not the case of IL-22 KO mice in which the IL-22 gene has been completely removed or the expression of the IL-22 gene has been inhibited. Specifically, to inhibit the activity of the IL-22 protein, an anti-IL-22 blocking antibody that binds to the IL-22 protein was used.

As a result, as shown in FIG. 42, it was confirmed that, when the activity of the IL-22 protein was inhibited, the proliferation of pancreatic cancer cells did not decrease, whereas when IL-10RB was inhibited by the anti-IL-10RB neutralizing antibody, the proliferation of pancreatic cancer cells significantly decreased.

Therefore, through this Experimental Example, it was confirmed that inhibition of IL-22 does not directly affect pancreatic cancer cells, but inhibition of IL-10RB in PBMCs may be induced only by inhibition of the IL-22 gene, resulting in reduction of pancreatic cancer cell proliferation. That is, it was confirmed that the control of IL-10RB can directly affect pancreatic cancer cells, and inhibition of the IL-22 gene can indirectly affect pancreatic cancer cells. It was confirmed that, although an inhibitor of the IL-22 gene induces an indirect effect, it may be used as an IL-10RB inhibitor, and thus the inhibitor of the IL-22 inhibitor may be used as an anticancer therapeutic agent that indirectly inhibits the proliferation of pancreatic cancer cells.

Although the present disclosure has been described in detail with reference to specific features, it will be apparent to those skilled in the art that this description is only of a preferred embodiment thereof, and does not limit the scope of the present disclosure. Thus, the substantial scope of the present disclosure will be defined by the appended claims and equivalents thereto.

DESCRIPTION OF REFERENCE NUMERALS

100: Sample receiving unit
200: Input unit
300: Diagnosis unit
400: Output unit

The invention claimed is:

1. A method for diagnosing and treating pancreatic cancer, comprising:

(a) measuring an expression level of interleukin-7 receptor alpha (IL-7RA), or a gene encoding IL-7RA, in peripheral blood mononuclear cells (PBMCs) obtained from a subject suspected of having pancreatic cancer by quantitative PCR to obtain a ΔCt value;

(b) diagnosing pancreatic cancer based on the ΔCt value being lower than a predetermined cutoff value, wherein the predetermined cutoff value is a ΔCt value obtained from PBMC samples of normal controls; and (c) treating the diagnosed pancreatic cancer by pancreatic a cancer surgery.

* * * * *